United States Patent
Zhong et al.

(10) Patent No.: US 10,160,767 B2
(45) Date of Patent: Dec. 25, 2018

(54) RAPAMYCIN DERIVATIVE, AND A PREPARATION METHOD, PHARMACEUTICAL COMPOSITION AND USE THEREOF

(71) Applicant: Institute of Pharmacology and Toxicology Academy of Military Medical Sciences P.L.A. China, Beijing (CN)

(72) Inventors: Wu Zhong, Beijing (CN); Song Li, Beijing (CN); Shuang Cao, Beijing (CN); Ruiyuan Cao, Beijing (CN); Junhai Xiao, Beijing (CN); Xinbo Zhou, Beijing (CN); Xingzhou Li, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/315,226

(22) PCT Filed: Jun. 3, 2015

(86) PCT No.: PCT/CN2015/080632
§ 371 (c)(1),
(2) Date: Nov. 30, 2016

(87) PCT Pub. No.: WO2015/184983
PCT Pub. Date: Dec. 10, 2015

(65) Prior Publication Data
US 2017/0253606 A1    Sep. 7, 2017

(30) Foreign Application Priority Data
Jun. 3, 2014  (CN) .......................... 2014 1 0242439

(51) Int. Cl.
| | |
|---|---|
| *C07D 491/18* | (2006.01) |
| *A61L 31/16* | (2006.01) |
| *A61L 31/08* | (2006.01) |
| *A61K 31/395* | (2006.01) |

(52) U.S. Cl.
CPC .......... *C07D 491/18* (2013.01); *A61K 31/395* (2013.01); *A61L 31/08* (2013.01); *A61L 31/16* (2013.01); *A61L 2300/426* (2013.01)

(58) Field of Classification Search
CPC ....... C07D 491/18; A61L 31/08; A61L 31/16; A61L 2300/426
See application file for complete search history.

(56) References Cited

U.S. PATENT DOCUMENTS

| | | |
|---|---|---|
| 4,650,803 A | 3/1987 | Stella et al. |
| 5,118,677 A | 6/1992 | Caufield |
| 5,162,333 A | 11/1992 | Failli et al. |
| 5,349,060 A | 9/1994 | Kao et al. |
| 5,378,696 A * | 1/1995 | Caufield .............. C07D 498/18 514/183 |
| 5,385,908 A | 1/1995 | Nelson et al. |
| 5,491,231 A | 2/1996 | Nelson et al. |

FOREIGN PATENT DOCUMENTS

| | | |
|---|---|---|
| EP | 1 181 938 A2 | 2/2002 |
| WO | WO 94/25468 A1 | 11/1994 |

(Continued)

OTHER PUBLICATIONS

International Search Report (ISR) for PCT/CN2015/080632; I.A. fd: Jun. 3, 2015, dated Sep. 9, 2015, State Intellectual Property Office of the P.R. China, Beijing, China.

(Continued)

*Primary Examiner* — Sarah Pihonak
*Assistant Examiner* — Jason Deck
(74) *Attorney, Agent, or Firm* — Sterne, Kessler, Goldstein & Fox P.L.L.C.

(57) ABSTRACT

The present invention pertains to the field of pharmaceutical chemicals, and relates to a rapamycin derivative of Formula I, and a preparation method, pharmaceutical composition and use thereof. The compounds of the present invention overcome the defects of rapamycin in terms of water solubility and metabolic properties, and some of the compounds have an in vitro anti-tumor activity superior to rapamycin, have less toxicity to normal cells than rapamycin, and have very good druggability.

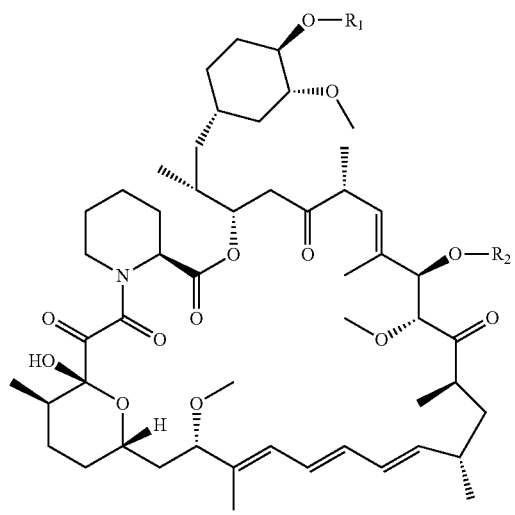

Rapamycin

12 Claims, 1 Drawing Sheet

(56) References Cited

FOREIGN PATENT DOCUMENTS

WO     WO 2009/105510 A1     8/2009
WO     WO 2012/004005 A1     1/2012

OTHER PUBLICATIONS

International Preliminary Report on Patentability (IPRP) including the Written Opinion of the International Searching Authority (PCT Rule 44bis) for PCT/CN2015/080632; I.A. fd: Jun. 3, 2015, dated Dec. 6, 2016, by the International Bureau of WIPO, Geneva, Switzerland.

The extended European search report including the supplementary European search report and the European search opinion, for EP Appl. No. 15803906.5, dated Dec. 4, 2017, European Patent Office, Munich, Germany.

First Office Action (dated Nov. 27, 2017), including First Search (dated Nov. 16, 2017), for CN Appl. No. 201410242439.5, The State Intellectual Property Office of the People's Republic of China, Beijing, China.

\* cited by examiner

RAPAMYCIN DERIVATIVE, AND A PREPARATION METHOD, PHARMACEUTICAL COMPOSITION AND USE THEREOF

TECHNICAL FIELD

The present invention pertains to the field of pharmaceutical chemicals, and relates to a rapamycin derivative, and a preparation method, pharmaceutical composition and use thereof.

BACKGROUND ART

Rapamycin is also called as Sirolimus, and was separated and obtained from *Streptomyces hygroscopicus* by Veniza et al in 1975. In 1989, Rapamycin entered clinical phase as a new immunosuppressor, and it was marketed in 1999. Later, the inhibition effect of rapamycin on T lymphocyte proliferation teaches using it to inhibit cancer cells, and it is found that it shows good antineoplastic activity, and this compound as an anticancer drug has been developed by Wyeth Company of the USA and is about to enter clinic phase.

The acting target of rapamycin in human body is mTOR (mammal rapamycin target protein). mTOR is an important component of PI3K-Akt-mTOR signal pathway. PI3K-Akt-mTOR signal pathway regulates proliferation- and apoptosis-related signal transduction pathways of tumor cells, so that on the one hand, proliferative activity of tumor cells is promoted to further enhance infiltration and metastasis abilities of tumor cells; and on the other hand, the acts on tumor apoptosis-related proteins promote activation of endogenous apoptosis inhibitors and/or expression and activation of apoptosis-inhibition-related protein kinases, thereby inhibiting apoptosis of tumor cells. Hence, PI3K-Akt-mTOR signal pathway may be the regulation core for tumor occurrence and development, so that mTOR is a key target for gene therapy of tumors.

In animal body, mTOR exists mainly in two complex forms, i.e., mTORC1 and mTORC2, in which mTORC1 (mTOR complex 1) consists of 4 parts: mTOR, raptor (regulatory associated protein of mTOR), mLST8, PRAS40 (Proline-rich AKT Substrate 40 kDa); while mTORC2 (mTOR complex2) consists of 5 parts: mTOR, rictor (raptor independent), mLST8, mSIN1 (mammalian stress-activated protein kinase interacting protein 1), Protor-1 (Proteinobserved with rictor-1). mTORC1 and mTORC2 involves almost all different upstream activators and downstream effectors, and they mutually harmonize and regulate together cell cycle progression. The downstream effectors of mTORC1 mainly include ribosome p70S6 kinase protein (S6 kinase 1, S6K1) and eukaryotic initiation factor 4E binding protein 1(4EBP1). By regulating 4EBP1 and S6K1 phosphorylation, mTORC1 influences translation initiation of specific mRNA, thereby regulating protein synthesis and regulating cell growth and proliferation, in which its major biological function is to regulate protein synthesis. When mTORC1 is stimulated by a factor such as a growth factor, it can promote cell growth and proliferation via activating downstream S6K1 (Thr389 site). Once mTORC1 in vivo is over-activated, downstream 4EBP1 and S6K1 would overexpressed, and then cell proliferation is out of control, and then excessive immune or cancers would occur. mTORC2 mainly takes part in construction of cytoskeletal proteins, and mTORC2 can upregulate Akt level via acting on Ser473 site of Akt. (TANG Yan, Research summary of mTOR inhibitors [J]. Organic Chemistry, 2011, 31(7): 1144-1154.)

The immunosuppression and antitumor mechanisms of rapamycin are mainly to inhibit mTORC1 via binding to cell receptor FKBP12, but rapamycin has very slight inhibition effects on mTORC2.

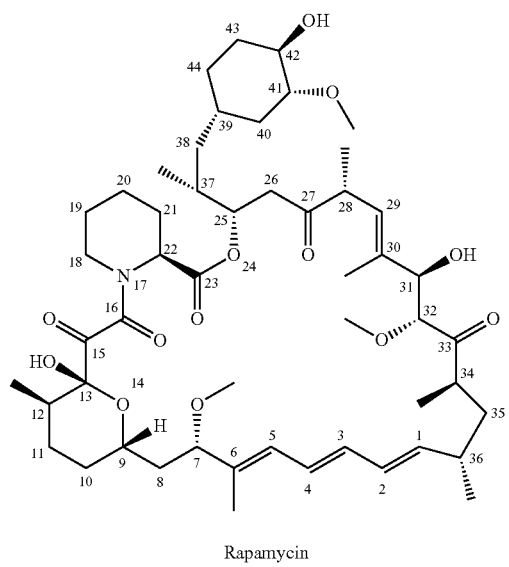 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

Rapamycin

Although rapamycin has potent anticancer activity, it has two severe defects: poor stability and poor water solubility. Rapamycin has a solubility of only 2.6 μg/ml in water, i.e., it is almost insoluble in water. After many years of research, it is found that modification of hydroxy at position 42 of rapamycin is a reliable way to improve physical and chemical properties of rapamycin, and some drugs in markets are based on this scheme.

Some rapamycin derivatives with position 42 substituted in markets are listed as follows:

Temsirolimus, of which the trade name is Torisel, is developed by Wyeth-Ayerst, and it is a rapamycin derivative with 42-acrylate, and is a prodrug of rapamycin. It is the earliest anticancer drug among rapamycin derivatives approved by FDA (2007). Temsirolimus is a first-line drug for treatment of advanced renal cell carcinoma (RCC) in patients, and it could extend median survival time by 3-6 months in early RCC patients. Temsirolimus can significantly inhibit T cell proliferation, its median inhibitory concentration ($IC_{50}$) is 0.8 nmol/L, and it can be used in combination with kinase inhibitors such as Sunitinib or Sorafenib.

Everolimus, of which the trade name is Zortress, is developed by Novartis Company, and is the first oral mTOR inhibitor, its chemical structure is 42-O-(2-hydroxyethyl)-rapamycin, the water solubility is superior to rapamycin, and it is rapidly hydrolyzed after entering human body. Experiments show that Everolimus has oral bioavailability of merely 15%-30%, and half-life of 16-19 h in human body. It firstly came into the market in Sweden in 2003, initially acted as only an immunosuppressor, and now it is approved to treat RCC, pancreatic neuroendocrine tumor (PNET) and subependymal giant cell astrocytoma (SEGA). FDA has approved that Everolimus oral tablets can be used for preventing adult kidney transplantation patients with lower or moderate immune risk from organ rejection response. Everolimus can be used simultaneously in combination with amount-reduced cyclosporine A and basiliximab and corticosteroids. The approved phase III test showed that Everolimus can prevent acute organ rejection and hold kidney function.

Ridaforolimus (Ariad/Merck Company) has modification at C43-position of rapamycin, which improves its solubility and PK value. As for its research work, its phase-III clinic test in treatment of metastatic soft-tissue or bone sarcomas had been completed. In comparison with placebo group, medication group had a mortality risk which was reduced by 28% (NCT00538239). In 2012, Ariad and Merck Company filed with FDA a new drug application of ridaforolimus, but FDA expert panel had doubt in its therapeutic effects, and thus there were some obstruction in application.

Zotarolimus (Medtroni Company) was approved by FDA in 2006 in Zotarolimus-coated coronary stent system (Endeavor), and in comparison with the bare-metal coronary stent group, the drug-coated group could effectively reduce death rate of arterial embolism, heart diseases and myocardial infarction in stent users.

Umiroliums (Biolimus, Biosensors Company) was approved in Europe in 2007 in Biolimus-coated coronary stent system, biolimus A9. It is more potent than rapamycin in terms of immunosuppression and anti-inflammatory activity, and it binders cell migration and proliferation by cell cycle arrest at G1, thereby preventing occurrence of vascular restenosis.

At present, it is still in need to develop new rapamycin derivatives.

CONTENTS OF INVENTION

With deep research and inventive work, the inventors of the present invention obtain a series of novel rapamycin carboxylic ester derivatives (compounds of Formula I) with quaternary ammonium salt structures, which tremendously overcome defects of rapamycin in terms of water solubility and metabolism (in which, the compound of Example 14 has a water solubility improved by 40,000 times in comparison with rapamycin), and some compounds are superior to rapamycin in vitro antitumor activity, have smaller toxicity on norm cells than rapamycin, and have a very good druggability. Thus, the following invention is provided.

One aspect of the present invention relates to a compound of Formula I, a pharmaceutically acceptable salt or hydrate thereof:

Formula I

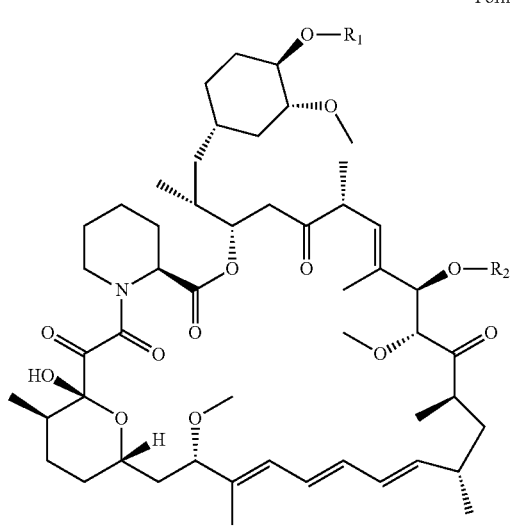

wherein, $R_1$ and $R_2$ are independently selected from H, A and B, and $R_1$, $R_2$ cannot be H simultaneously;

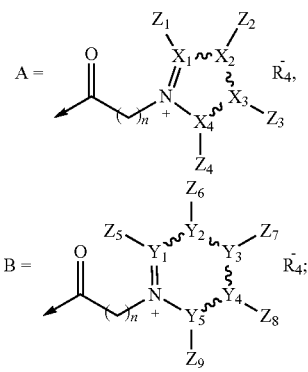

wherein, in Formula A or Formula B, arrows refer to sites where A or B links to mother ring of Formula I;

n independently is 1, 2, 3, 4, 5, 6 or 7;

$R_4$ is independently selected from fluorine, chlorine, bromine, iodine, nitro, and cyano;

$X_1$, $X_2$, $X_3$, $X_4$, $Y_1$, $Y_2$, $Y_3$, $Y_4$, $Y_5$ are independently selected from C, S, O, N and Se atoms;

$X_1 \sim X_2$, $X_2 \sim X_3$, $X_3 \sim X_4$, $Y_1 \sim Y_2$, $Y_2 \sim Y_3$, $Y_3 \sim Y_4$, $Y_4 \sim Y_5$ are independently single bond or double bond; ($X_1 \sim X_2$ and $Y_1 \sim Y_2$ do not from double bond, which is well-known in the art.)

$Z_1$, $Z_2$, $Z_3$, $Z_4$, $Z_5$, $Z_6$, $Z_7$, $Z_8$, $Z_9$ are independently selected from hydrogen atom, hydroxy, aldehyde group, carboxyl, amino, cyano, halogen, $C_1$-$C_6$ alkyl, $C_3$-$C_{10}$ cycloalkyl, $C_1$-$C_6$ alkoxy, $C_1$-$C_6$alkylthiol, $C_3$-$C_{10}$ cycloalkoxy, $C_1$-$C_6$ alkenyl, eneynylheterocyclic ring, heterocycloalkyl, substituted heterocycloalkyl, aromatic ring, aromatic heterocyclic ring, benzo-aromatic heterocyclic ring, wherein the $C_1$-$C_6$ alkyl, aromatic ring, aromatic heterocyclic ring, benzo-aromatic heterocyclic ring are not substituted or substituted with 1, 2, 3, 4 or 5 substituents independently selected from: —F, —Cl, —Br, —I, nitro, hydroxy, amino, cyano, $C_1$-$C_6$ alkylthiol, $C_1$-$C_6$ alkyl, $C_1$-$C_6$ alkenyl, $C_1$-$C_6$ alkynyl and $C_1$-$C_6$ alkoxy.

Preferably, N atom together with $X_1$, $X_2$, $X_3$, $X_4$, or with $Y_1$, $Y_2$, $Y_3$, $Y_4$, $Y_5$ form a heterocyclic structure; preferably, a stable heterocyclic structure.

As for the compound of Formula I according to any one of items of the present invention, a pharmaceutically acceptable salt or hydrate thereof, preferably:

$Z_1$, $Z_2$, $Z_3$, $Z_4$, $Z_5$, $Z_6$, $Z_7$, $Z_8$, $Z_9$ are independently selected from hydrogen atom, hydroxy, aldehyde group, carboxyl, amino, cyano, halogen, $C_1$-$C_3$ alkyl, $C_3$-$C_5$ cycloalkyl, $C_1$-$C_3$ alkoxy, $C_1$-$C_3$ alkylthiol, $C_3$-$C_5$ cycloalkoxy, and $C_1$-$C_3$ alkyl-enyl.

As for the compound of Formula I according to any one of items of the present invention, a pharmaceutically acceptable salt or hydrate thereof, preferably:

in Formula A, N atom together with $X_1$, $X_2$, $X_3$, $X_4$ form a thiazole ring, and/or in Formula B, N atom together with $Y_1$, $Y_2$, $Y_3$, $Y_4$, $Y_5$ form a pyridine ring.

As for the compound of Formula I according to any one of items of the present invention, a pharmaceutically acceptable salt or hydrate thereof, preferably:

$Z_1$, $Z_2$, $Z_3$, $Z_4$, $Z_5$, $Z_6$, $Z_7$, $Z_8$, $Z_9$ are independently selected from hydrogen atom, hydroxyl and methyl.

As for the compound of Formula I according to any one of items of the present invention, a pharmaceutically acceptable salt or hydrate thereof, preferably:

$R_1$ and $R_2$ are independently selected from H, carbonylmethyl-(4-methyl-thiazole $R_4$ salt-3-yl), carbonylmethyl-(4,5-dimethyl-thiazole $R_4$ salt-3-yl), carbonylmethyl-(pyridine $R_4$ salt-1-yl), carbonylmethyl-(3-hydroxy-pyridine $R_4$ salt-1-yl), carbonylmethyl-(3-methyl-pyridine $R_4$ salt-1-yl) and carbonylmethyl-(4-methyl-pyridine $R_4$ salt-1-yl), wherein $R_4$ is independently selected from fluorine, chlorine, bromine, iodine, nitro and cyano; and $R_1$, $R_2$ cannot be H simultaneously.

As for the compound of Formula I according to any one of items of the present invention, a pharmaceutically acceptable salt or hydrate thereof, preferably:

$R_1$ and $R_2$ are independently selected from H, carbonylmethyl-(4-methyl-thiazole bromide salt-3-yl), carbonylmethyl-(4, 5-dimethyl-thiazole bromide salt-3-yl), carbonylmethyl-(pyridine bromide salt-1-yl), carbonylmethyl-(3-hydroxy-pyridine bromide salt-1-yl), carbonylmethyl-(3-methyl-pyridine bromide salt-1-yl) and carbonylmethyl-(4-methyl-pyridine bromide salt-1-yl);

and $R_1$, $R_2$ cannot be H simultaneously.

In one embodiment, the compounds, their pharmaceutically acceptable salts or their hydrates of the present invention are selected from Table 1.

TABLE 1

Some compounds of the present invention

| Example/Compound No. | Name | Strucure Formula |
|---|---|---|
| 1 | 31,42-O-carbonylmethyl-(4-methyl-thiazole bromide salt-3-yl)-rapamycin | 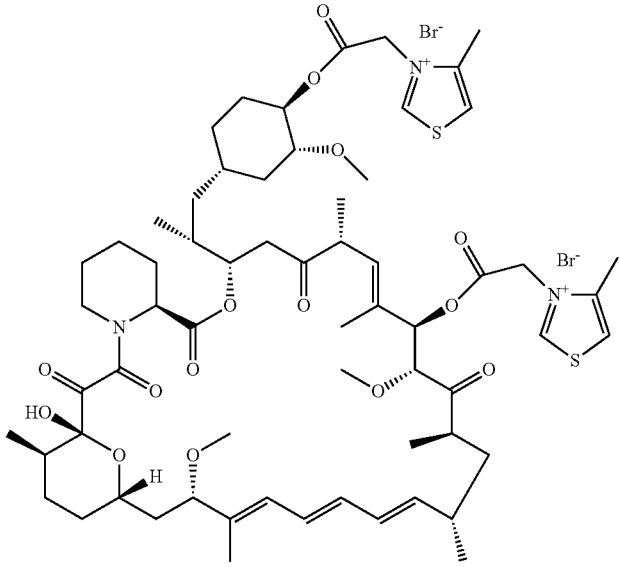<br>Compound 1 |
| 2 | 42-O-carbonylmethyl-(4-methyl-thiazole bromide salt-3-yl)-rapamycin | 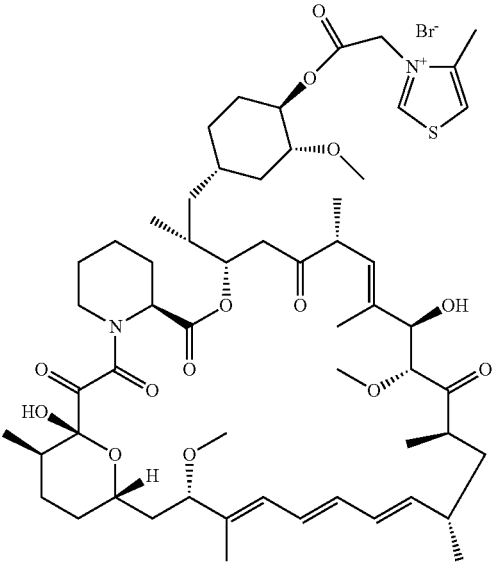 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)C[n+]3cscc3C)[C@H](OC)C2)CC(=O)[C@H](C)/C=C(\C)[C@@H](O)[C@@H](OC)C(=O)[C@H](C)C[C@H](C)/C=C/C=C/C=C/1C ; [Br-]]<br>Compound 2 |

TABLE 1-continued
Some compounds of the present invention
| Example/ Compound No. | Name | Strucure Formula |
|---|---|---|
| 3 | 31-O-carbonylmethyl-(4-methyl-thiazole bromide salt-3-yl)-rapamycin | 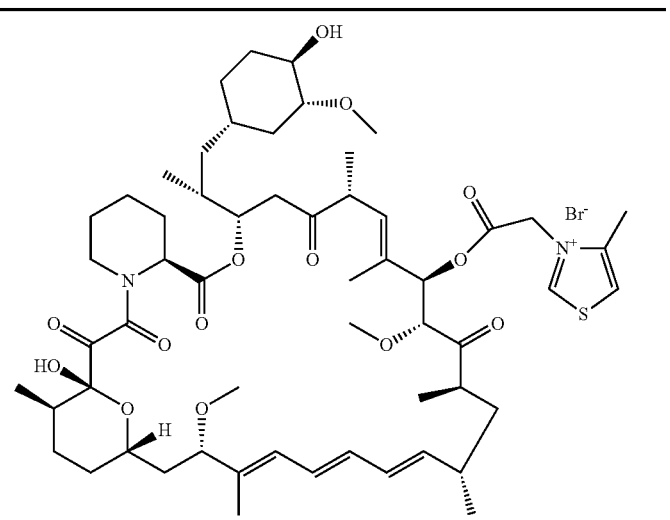<br>Compound 3 |
| 4 | 31,42-O-carbonylmethyl-(4,5-dimethyl-thiazole bromide salt-3-yl)-rapamycin | 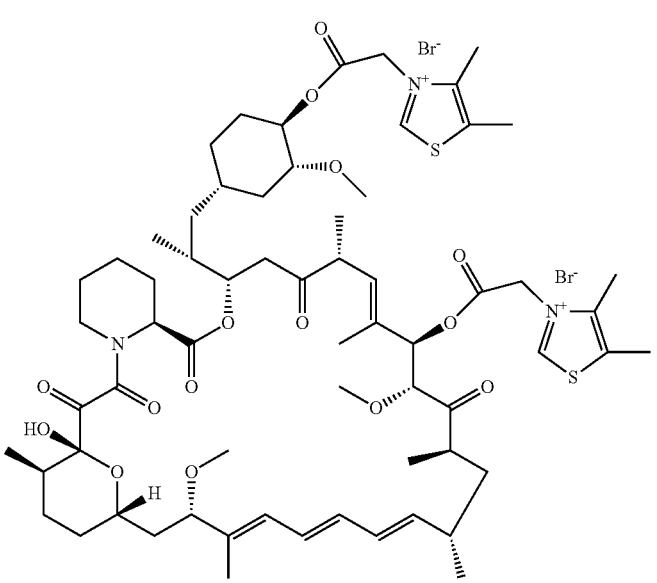<br>Compound 4 |

TABLE 1-continued

Some compounds of the present invention

| Example/ Compound No. | Name | Structure Formula |
|---|---|---|
| 5 | 42-O-carbonylmethyl-(4,5-dimethyl-thiazole bromide salt-3-yl)-rapamycin | Compound 5 |
| 6 | 31-O-carbonylmethyl-(4,5-dimethyl-thiazole bromide salt-3-yl)-rapamycin | Compound 6 |

TABLE 1-continued
Some compounds of the present invention
| Example/ Compound No. | Name | Strucure Formula |
|---|---|---|
| 7 | 31,42-O-carbonylmethyl-(pyridine bromide salt-1-yl)-rapamycin | 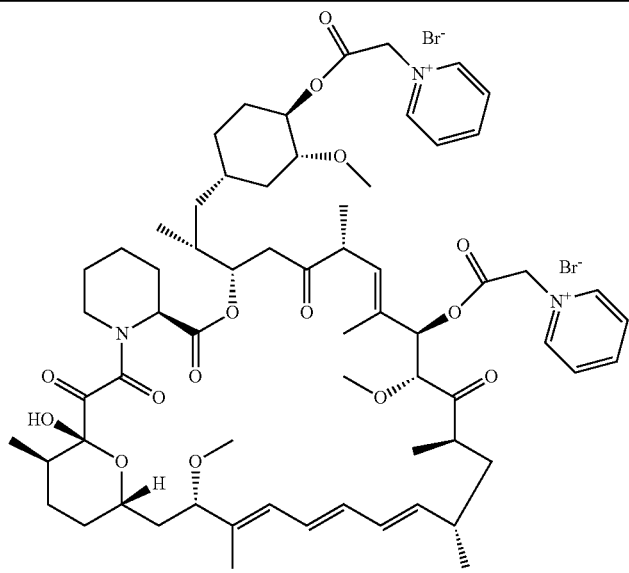<br>Compound 7 |
| 8 | 31,42-O-carbonylmethyl-(3-hydroxy-pyridine bromide salt-1-yl)-rapamycin | 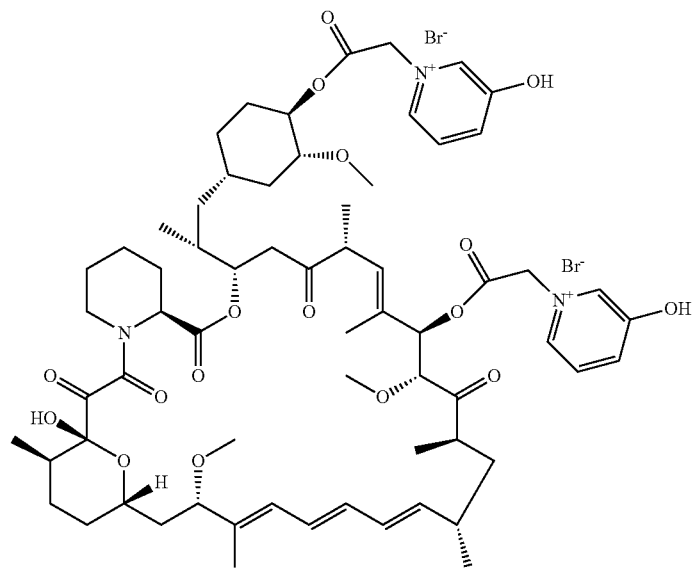 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)C[n+]3cccc(O)c3)[C@H](OC)C2)CC(=O)[C@H](C)/C=C(\C)[C@@H](OC(=O)C[n+]2cccc(O)c2)[C@@H](OC)C(=O)[C@H](C)C[C@H](C)/C=C/C=C/C=C/1C ; [Br-] ; [Br-]]<br>Compound 8 |

TABLE 1-continued

Some compounds of the present invention

| Example/Compound No. | Name | Strucure Formula |
|---|---|---|
| 9 | 31,42-O-carbonylmethyl-(3-methyl-pyridine bromide salt-1-yl)-rapamycin | Compound 9 |
| 10 | 42-O-carbonylmethyl-(pyridine bromide salt-1-yl)-rapamycin | Compound 10 |

TABLE 1-continued
Some compounds of the present invention
| Example/<br>Compound<br>No. | Name | Strucure Formula |
|---|---|---|
| 11 | 42-O-carbonylmethyl-(3-methyl-pyridine bromide salt-1-yl)-rapamycin | 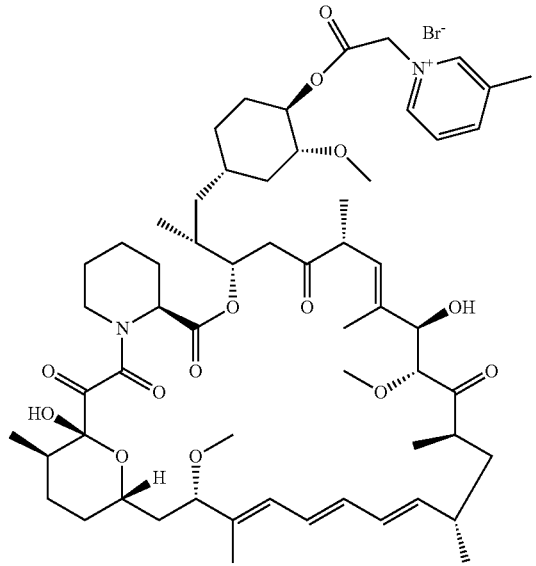<br>Compound 11 |
| 12 | 42-O-carbonylmethyl-(3-hydroxy-pyridine bromide salt-1-yl)-rapamycin | 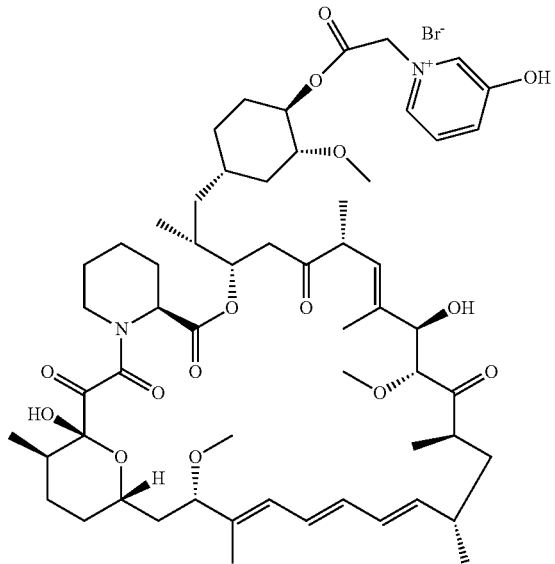 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)C[n+]3cccc(O)c3)[C@H](OC)C2)CC(=O)[C@H](C)/C=C(\C)[C@@H](O)[C@@H](OC)C(=O)[C@H](C)C[C@H](C)/C=C/C=C/C=C/1C ; [Br-]]<br>Compound 12 |

TABLE 1-continued
Some compounds of the present invention
| Example/<br>Compound<br>No. | Name | Strucure Formula |
|---|---|---|
| 13 | 42-O-carbonylmethyl-(4-methyl-pyridine bromide salt-1-yl)-rapamycin | 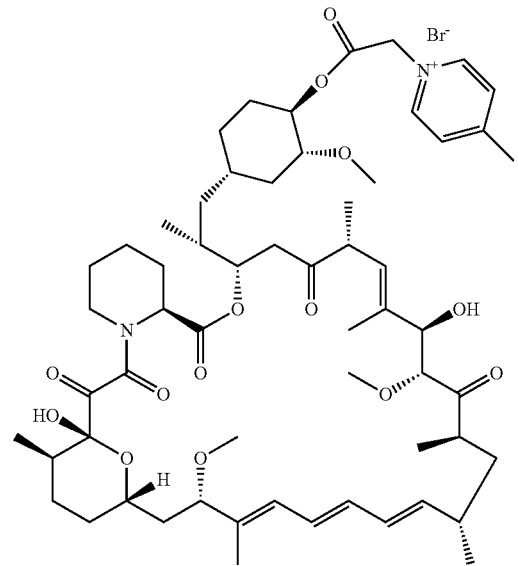<br>Compound 13 |
| 14 | 31,42-O-carbonylmethyl-(4-methyl-pyridine bromide salt-1-yl)-rapamycin | 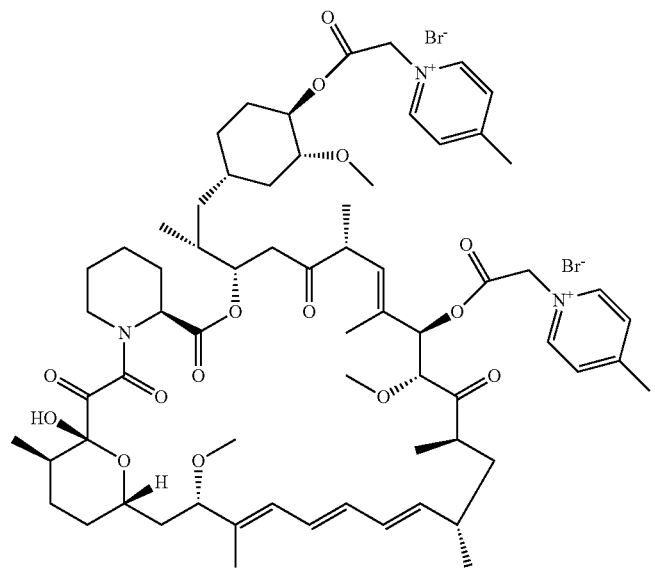<br>Compound 14 |

TABLE 1-continued
Some compounds of the present invention
| Example/ Compound No. | Name | Strucure Formula |
|---|---|---|
| 15 | 31-O-carbonylmethyl-(3-methyl-pyridine bromide salt-1-yl)-rapamycin | 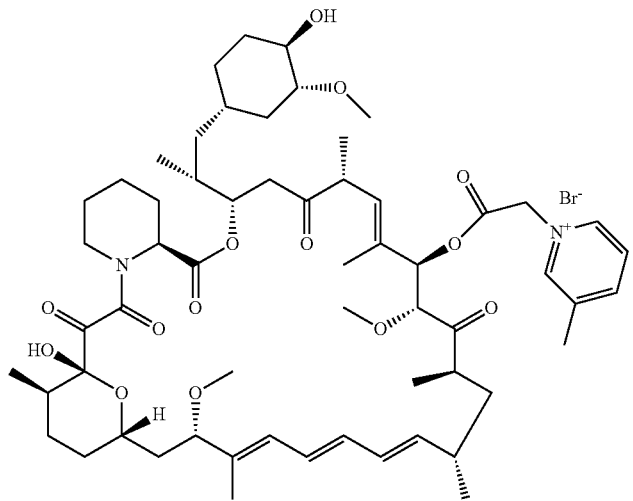 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](OC(=O)C[n+]2cccc(C)c2)[C@@H](OC)C(=O)[C@H](C)C[C@H](C)/C=C/C=C/C=C/1C ; [Br-]]<br>Compound 15 |
| 16 | 31-O-carbonylmethyl-(pyridine bromide salt-1-yl)-rapamycin | 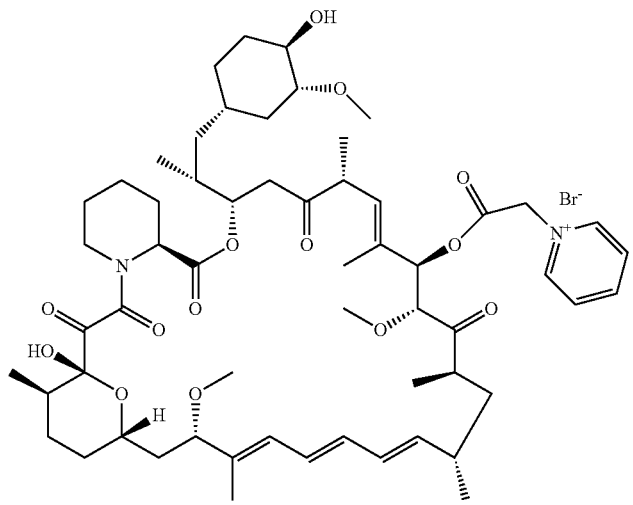 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](OC(=O)C[n+]2ccccc2)[C@@H](OC)C(=O)[C@H](C)C[C@H](C)/C=C/C=C/C=C/1C ; [Br-]]<br>Compound 16 |

TABLE 1-continued

Some compounds of the present invention

| Example/ Compound No. | Name | Strucure Formula |
|---|---|---|
| 17 | 31-O-carbonylmethyl-(4-methyl-pyridine bromide salt-1-yl)-rapamycin | 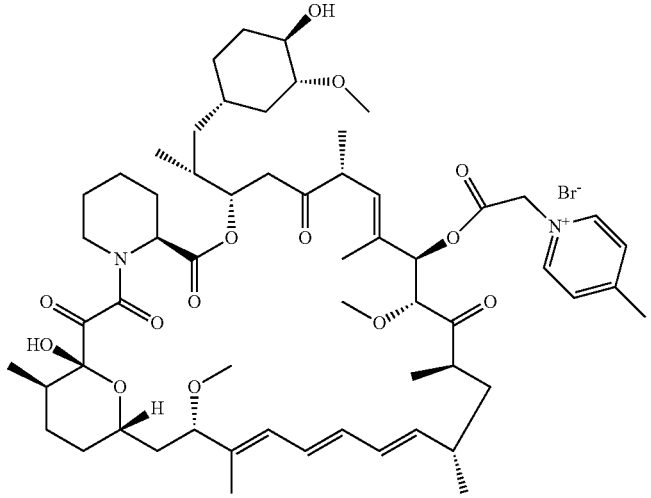 Compound 17 |

Another aspect of the present invention relates to a method for preparing the compound of Formula I according to any one of items of the present invention, which comprises steps of any one of the following processes (1) to (3):

Process (1): Preparation of Compounds of Formula I with Position 31,42 Bis-Substituted

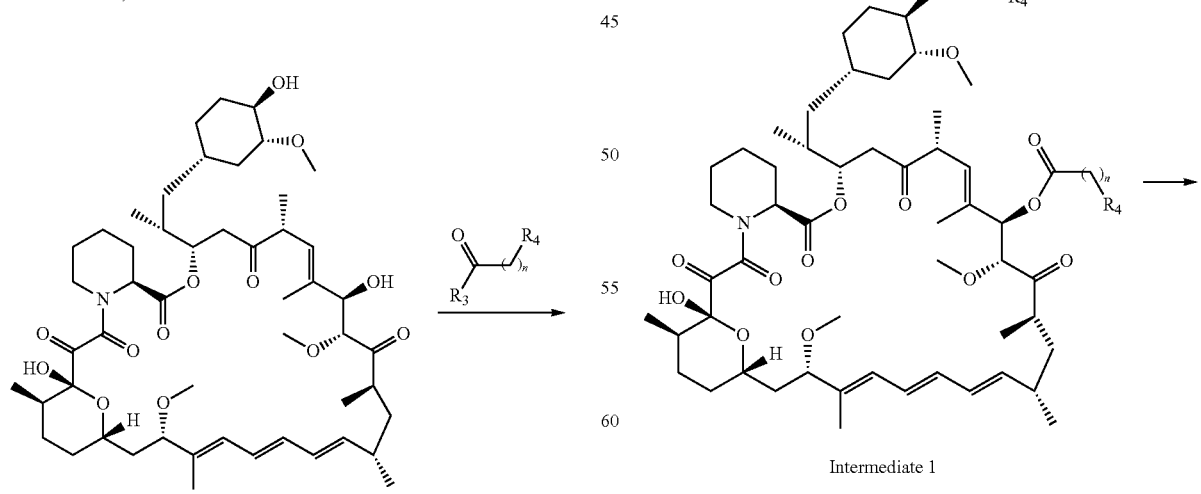

Intermediate 1

23
-continued
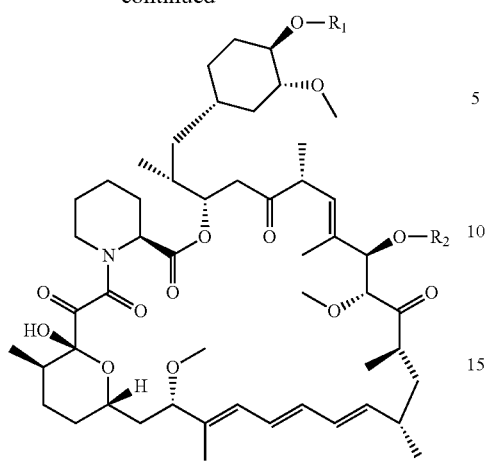
Process (2): Preparation of Compounds of Formula I with Position 42 Mono-Substituted
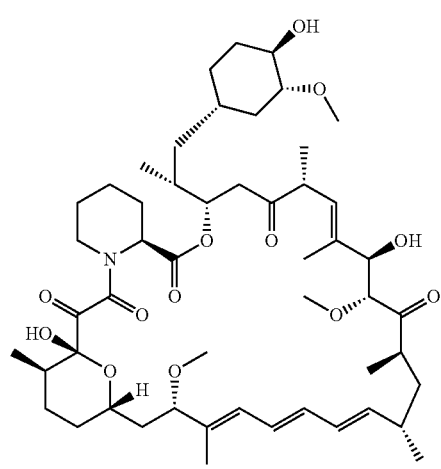
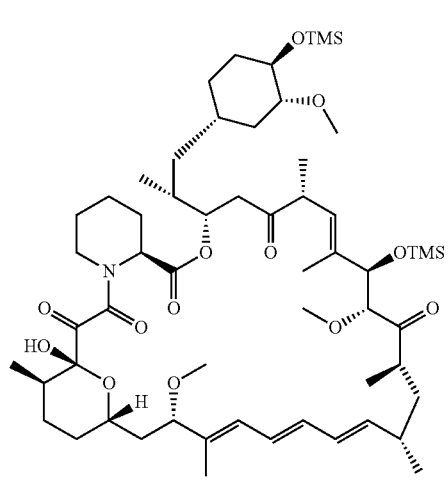
Intermediate 2
24
-continued
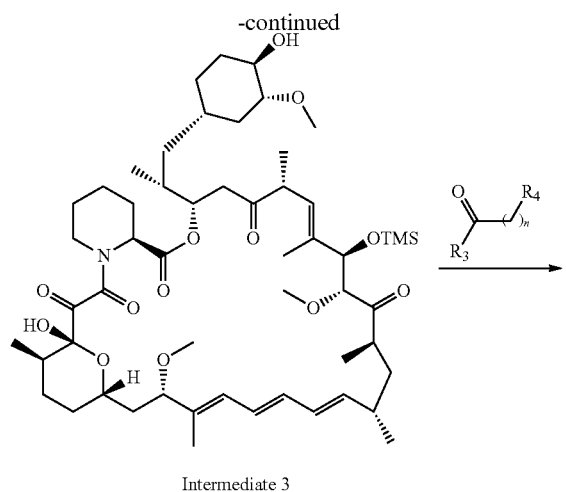
Intermediate 3
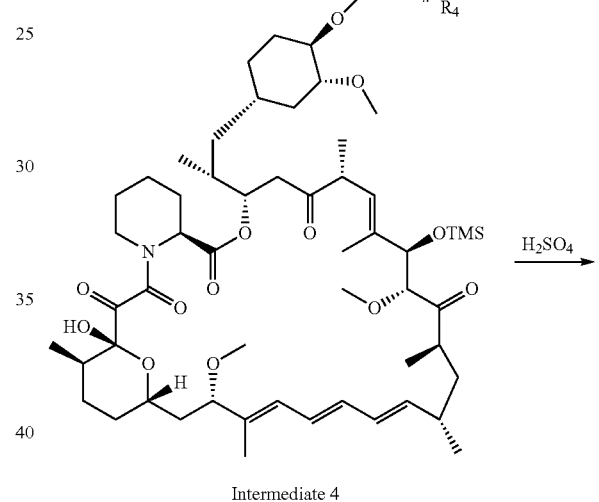
Intermediate 4
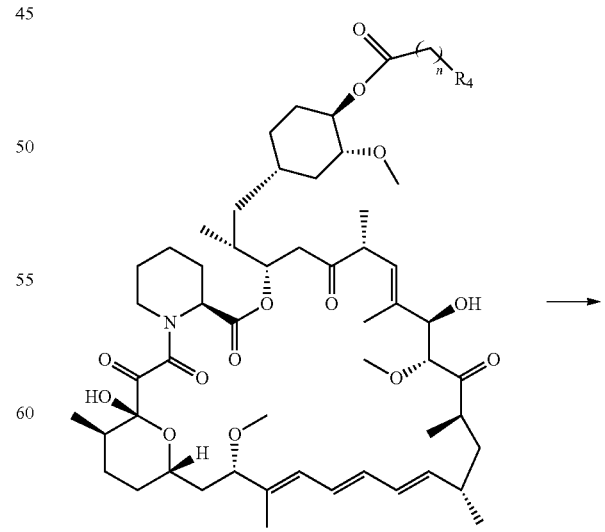
Intermediate 5

25
-continued
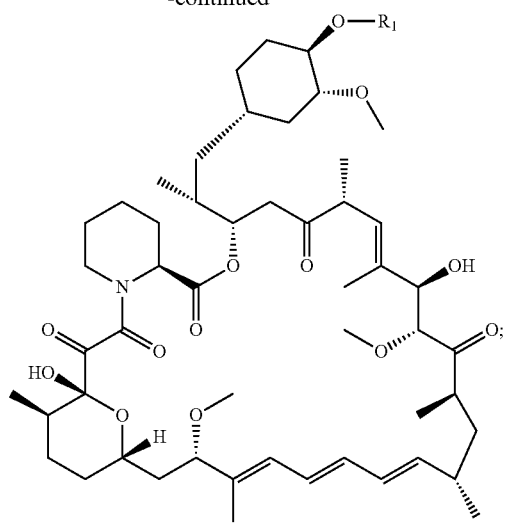
26
-continued
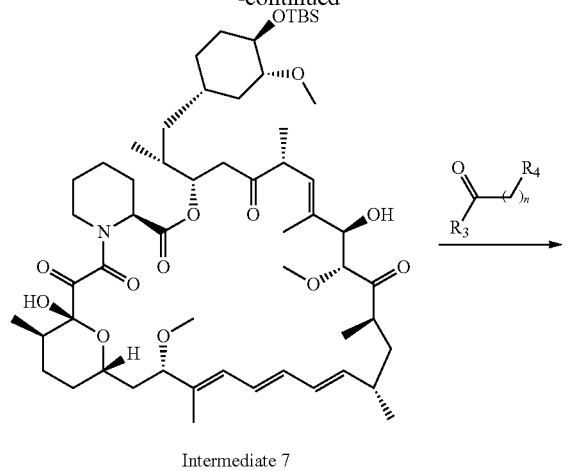
Intermediate 7
Process (3): Preparation of Compounds of Formula I with Position 31 Mono-Substituted
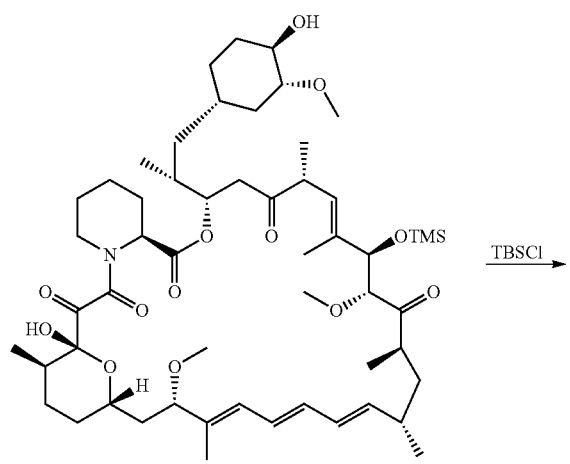
Intermediate 6
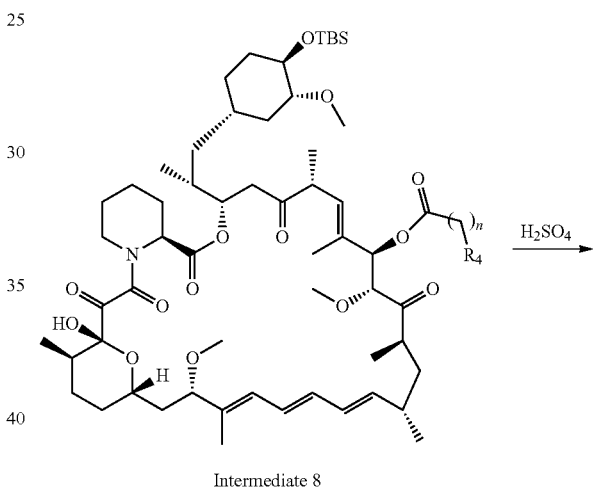
Intermediate 8
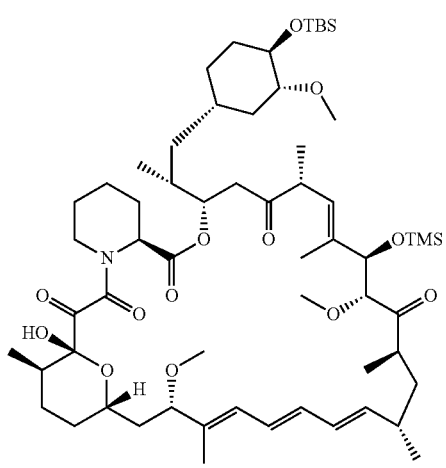
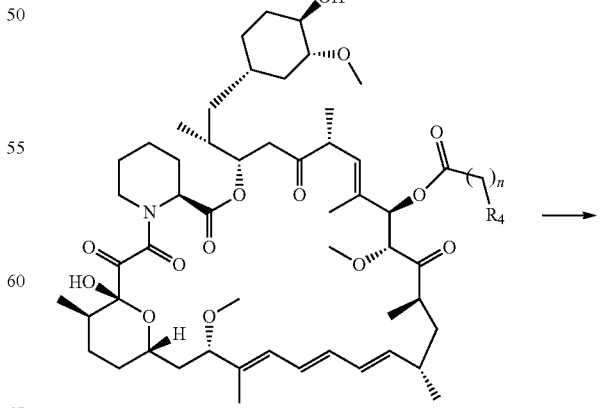
Intermediate 9

-continued

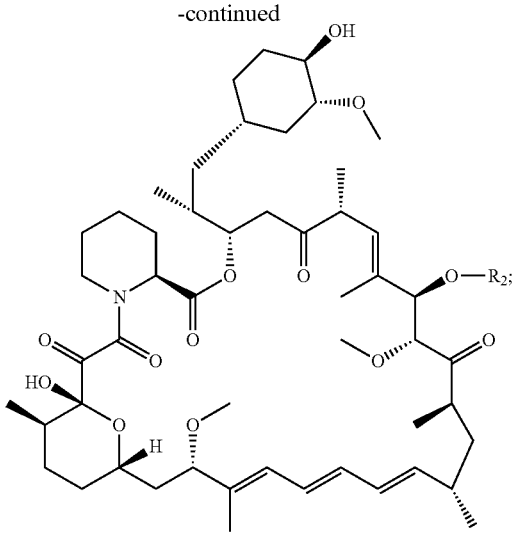

wherein in the above processes (1) to (3), $R_3$ is independently selected from F, Cl, Br and I;

the meanings of other notations are independently the same as stated in any one of the above items.

In Process (1), rapamycin is firstly reacted with acyl halide to generate 31- and 42-bis-esterification product (Intermediate 1), then the product is reacted with heterocyclic ring to generate quaternary ammonium salt type rapamycin derivatives with position 31, 42 bis-substituted.

In Process (2), rapamycin firstly reacts with sufficient trimethylcholosilane to generate Intermediate 2, then its ether bond at position 31 is hydrolyzed in the presence of an acid to generate Intermediate 3, then this intermediate is substituted at position 42 with halogenated acryl halide to obtain Intermediate 4, then the trimethylsilyl ether at position 31 is hydrolyzed with an acid to obtain 42-mono-esterification product (Intermediate 5); finally, Intermediate 5 is reacted with azacyclic ring to generate quaternary ammonium salt type rapamycin derivatives with position mono-substituted.

In Process (3), Intermediate 3 is substituted at position 42 with tert-butyldimethylchlorosilane to obtain Intermediate 6; subsequently, trimethylsilyl ether at position 31 is hydrolyzed with an acid to obtain Intermediate 7; Intermediate 7 reacts with halogenated acyl halide to obtain Intermediate 8; then tert-butyldimethylsilyl ether is hydrolyzed under acidic condition to obtain Intermediate 9; finally, Intermediate 9 is reacted with azacyclic ring to generate quaternary ammonium salt type rapamycin derivatives with position 31 mono-substituted.

In the last step of the Process (1), i.e., in the reaction from Intermediate 1 to the final product in Process (1), a reaction reagent (hereinafter cited as R5) can be added.

In the last step of the Process (2), i.e., in the reaction from Intermediate 5 to the final product in Process (2), a reaction reagent (hereinafter cited as R5) can be added.

In the last step of the Process (3), i.e., in the reaction from Intermediate 9 to the final product in Process (3), a reaction reagent (hereinafter cited as R5) can be added.

The reagent $R_5$ is independently selected from 5-membered heterocyclic compound, and 6-membered heterocyclic compound; preferably, selected from thiazole, pyridine, thiazole substituted with one or more $C_1$-$C_6$ alkyl, pyridine substituted with one or more $C_1$-$C_6$ alkyl, thiazole substituted with one or more halogen atoms, and pyridine substituted with one or more halogen atoms; more preferably, selected from 4-methylthiazole, 4, 5-dimethylthiazole, pyridine, 3-hydroxypyridine, 3-methylpyridine and 4-methylpyridine.

Another aspect of the present invention relates to a pharmaceutical composition, which comprises the compound of any one of items of the preset invention, a pharmaceutically acceptable salt or hydrate thereof, and optionally a pharmaceutically acceptable excipient.

The compounds of the present invention all have very good water solubility, are convenient to prepare various dosage forms. When used for oral administration, the compound of the present invention can be processed in any preparation dosage forms suitable for oral administration, including but not being limited to tablets, capsules, aqueous solutions or aqueous suspensions, in which carriers of tablets usually include lactose and corn starch, and lubricants such as magnesium stearate may also be added. Diluents of capsules usually include lactose and dry corn starch. In aqueous suspensions, active ingredient is usually used together with suitable emulsifying agents and suspending agents. If required, the above dosage forms for oral administration may further be added with some sweeting agents, fragrances or coloring agents.

The compound of the present invention can also be administered in sterile injection dosage form, including sterile injection water or oil suspension or sterile injection solution, wherein the usable carriers and solvents include water, Ringer's solution and isotonic NaCl solution.

The compound according to any one of items of the present invention, a pharmaceutically acceptable salt or hydrate thereof, or the pharmaceutical composition of the present invention, can be used as a medicament.

The compound according to any one of items of the present invention, a pharmaceutically acceptable salt or hydrate thereof, or the pharmaceutical composition of the present invention, can be used for suppressing immune, inhibiting mTOR, inhibiting mTORC1, inhibiting PI3K-Akt-mTOR signal pathway, inhibiting T lymphocyte proliferation, anti-tumor, promoting tumor cell apoptosis, allowing cell cycle arrest at G1, reducing arterial embolism, anti-aging, anti-Alzheimer's disease, preventing organ rejection, anti-inflammatory or anti-microbial; preferably, the anti-tumor refers to treatment and/or prophylaxis and/or adjuvant therapy of kidney cancer, lymphoma, lung cancer, liver cancer, breast cancer, neuroendocrine cancer, uterine sarcoma or gastric cancer.

The present invention further relates to a method for treatment and/or prophylaxis and/or adjuvant therapy of kidney cancer, lymphoma, lung cancer, liver cancer, breast cancer, neuroendocrine cancer, uterine sarcoma or gastric cancer, comprising a step of using an effective amount of the compound according to any one of items of the present invention, a pharmaceutically acceptable salt or hydrate thereof, or the pharmaceutical composition of the present invention.

The administration dosage of the compound of the present invention, a pharmaceutically acceptable salt or hydrate thereof, or the pharmaceutical composition of the present invention, depends on many factors, for examples, properties and severities of diseases to which the treatment or adjuvant therapy is applied, gender, age, body weight and individual responses of patients or animals, specific compounds to be used, administration routes and times, etc. The dosage can be administrated in a single dosage form or in 2, 3, 4 dosage forms.

Further another aspect of the present invention relates to a use of the compound according to any one of items of the present invention, a pharmaceutically acceptable salt or hydrate thereof, or the pharmaceutical composition of the present invention, in the manufacture of an immunosuppressant, a mTOR inhibitor, a mTORC1 inhibitor, a drug for inhibiting PI3K-Akt-mTOR signal pathway, a drug for inhibiting T lymphocyte proliferation, an antitumor drug, drug for promoting tumor cell apoptosis, a drug allowing cell cycle arrest at G1, a drug for preventing organ rejection, a drug for lowering arterial embolism, an anti-aging drug, drug against Alzheimer's disease, an anti-inflammatory drug or an antibacterial drug; preferably, the antitumor drug is a medicament for treatment and/or prophylaxis and/or adjuvant therapy of kidney cancer, lymphoma, lung cancer, liver cancer, breast cancer, neuroendocrine cancer, uterine sarcoma or gastric cancer.

Further another aspect of the present invention relates to a method for suppressing immune, inhibiting mTOR, inhibiting mTORC1, inhibiting PI3K-Akt-mTOR signal pathway, inhibiting T lymphocyte proliferation, combating tumors, promoting tumor cell apoptosis, allowing cell cycle arrest at G1, lowering arterial embolism, combating aging, combating Alzheimer's disease, preventing organ rejection, combating inflammation or combating microbes in vivo or in vitro, comprising a step of using an effective amount of the compound according to any one of items of the present invention, a pharmaceutically acceptable salt or hydrate thereof, or the pharmaceutical composition of the present invention.

In one embodiment of the present invention, the "in vitro" method is for non-therapeutic purpose.

Further another aspect of the present invention relates to a coronary stent, comprising a drug coating comprising the compound according to any one of items of the present invention, a pharmaceutically acceptable salt or hydrate thereof, or the pharmaceutical composition of the present invention.

The present invention further relates to a use of the compound according to any one of items of the present invention, a pharmaceutically acceptable salt or hydrate thereof, or the pharmaceutical composition of the present invention, in the manufacture of the coronary stent.

The present invention further relates to a method for preparing the coronary stent, comprising a step of using an effective amount of the compound according to any one of items of the present invention, a pharmaceutically acceptable salt or hydrate thereof, or the pharmaceutical composition of the present invention.

In the present invention,

The term "$C_1$-$C_6$ alkyl" refers to a straight or branched alkyl having 1-4 carbon atoms, for example, methyl, ethyl, propyl, isopropyl, n-butyl, sec-butyl, tert-butyl, pentyl, 2-pentyl, isopentyl, neopentyl, hexyl, 2-hexyl, 3-hexyl, etc.; $C_1$-$C_4$ alkyl, $C_1$-$C_3$ alkyl or $C_1$-$C_2$ alkyl can be interpreted similarly. Specific alkyl can be $C_1$-$C_4$ alkyl, $C_1$-$C_3$ alkyl or $C_1$-$C_2$ alkyl.

The term "$C_1$-$C_6$ alkoxy" refers to a straight or branched alkoxy having 1-6 carbon atoms, for example, methoxy, ethoxy, propoxy, isopropoxy, n-butoxy, sec-butoxy, tert-butoxy, pentoxy, 2-pentoxy, isopentoxy, neo-pentoxy, hexyloxy, 2-hexyloxy, 3-hexyloxy, etc.; $C_1$-$C_4$ alkoxy, $C_1$-$C_3$ alkoxy or $C_1$-$C_2$ alkoxy can be interpreted similarly. Specific alkoxy is $C_1$-$C_4$ alkoxy, $C_1$-$C_3$ alkoxy or $C_1$-$C_2$ alkoxy.

The term "$C_1$-$C_6$alkylthio" can be interpreted in a way similar to "$C_1$-$C_6$ alkoxy", which difference lies in oxygen atom is replaced with sulfur atom.

The term "$C_3$-$C_{10}$cycloalkyl" refers to saturated carbocyclic group having 3-10 carbon atoms. The cycloalkyl can be monocyclic or polycyclic fused system, and can be fused on aromatic ring. Examples of these groups include cyclopropyl, cyclobutyl, cyclopentyl and cyclohexyl. In the text, the cycloalkyl is not substituted or substituted with various groups at one or more substitutable positions. For example, these cycloalkyls can be substituted with following groups: $C_1$-$C_6$ alkyl, $C_1$-$C_6$ alkoxy, cyano, halogen, hydroxy, amino, nitro, mono($C_1$-$C_6$) alkylamino, di($C_1$-$C_6$) alkylamino, $C_2$-$C_6$ alkenyl, $C_2$-$C_6$ alkynyl, $C_1$-$C_6$ halogenated alkyl, $C_1$-$C_6$ halogenated alkoxy. $C_3$-$C_6$ cycloalkyl can be interpreted similarly.

The term "$C_3$-$C_{10}$cycloalkoxy" refers to saturated cycloalkoxy group having 3-10 carbon atoms. The cycloalkoxy can be monocyclic or polycyclic fused system, and can be fused on an aromatic ring. Examples of these groups include cyclopropoxy, cycloprobutoxy, cyclopentoxy and cyclohexyloxy. In the test, the cycloalkoxy is not substituted or substituted with various groups at one or more substitutable positions. For example, these cycloalkoxys can be optionally substituted with following groups: $C_1$-$C_6$ alkyl, $C_1$-$C_6$ alkoxy, cyano, halogen, hydroxy, amino, nitro, mono($C_1$-$C_6$) alkylamino, di($C_1$-$C_6$) alkylamino, $C_2$-$C_6$ alkenyl, $C_2$-$C_6$ alkynyl, $C_1$-$C_6$ halogenated alkyl, $C_1$-$C_6$ halogenated alkoxy, $C_3$-$C_6$cycloalkoxy can be interpreted similarly.

The term "$C_2$-$C_6$ alkenyl" refers to alkenyl having 2-6 carbon atoms and at least one double bond, and includes ethenyl, propenyl, 1-buten-3-yl, 1-penten-3-yl, 1-hexen-5-yl; $C_3$-$C_5$ alkenyl can be interpreted similarly. $C_3$-$C_5$ alkenyl is preferred.

The term "$C_2$-$C_6$ alkynyl" refers to hydrocarbonyl having 2-6 carbon atoms and at least one triple bond, and includes ethynyl, propynyl, butynyl, pentyn-2-yl; $C_3$-$C_5$ alkynyl can be interpreted similarly. $C_3$-$C_5$ alkynyl is preferred.

The term "halogen" or "halogen atom" refers to fluorine, chlorine, bromine, or iodine atom.

The term "aromatic ring" or "aryl" refers to aromatic carbocyclic group having monocyclic ring (e.g., phenyl), polycyclic ring (e.g., biphenyl) or polycyclic fused rings with at least one aromatic ring (e.g., 1,2,3,4-tetrahydronaphthyl, naphthyl), which can be optionally mono-, bis- or tri-substituted with halogen, lower alkyl, lower alkoxy, trifluoromethyl, aryl, heteroaryl and hydroxy.

The term "arylalkyl" refers to alkyl (as defined above) substituted with one or more aryl groups (as defined above). Preferably, aryl alkyl is aryl-$C_1$-$C_3$ alkyl. Examples include benzyl, phenylethyl.

The term "aromatic heterocyclic ring" or "heteroaryl" refers to 5-, 6- or 7-membered monocyclic or polycyclic aromatic ring system, including fused ring system comprising 5-10 atoms (in which at least one ring is aromatic ring), and the ring system contains at least one and at most four heteroatoms selected from nitrogen, oxygen or sulfur. Examples of heteroaryl is pyridinyl, imidazolyl, pyrimidyl, pyrazolyl, triazolyl, pyrazinyl, tetrazyl, furyl, thienyl, isoxazole, thiazolyl, oxazolyl, isothiazolyl, pyrrolyl, quinolone ring, isoquinolone ring, indole ring, benzo-imidazole, benzo-furan ring, benzo-thiophene, benzo-thiazole ring, pyridazine ring, etc., which is optionally mono-, bis- or tri-substituted with halogen, lower alkyl, lower alkoxy, trifluoromethyl, aryl, heteroaryl and hydroxy.

The term "heterocyclic ring" or "heterocyclic group" refers to 5-, 6- or 7-membered monocyclic or polycyclic ring system, including fused ring system comprising 4-10 atoms, and the ring system contains at least one and at most four heteroatoms selected from nitrogen, oxygen or sulfur, with proviso that the ring group does not contain two adjacent O or S atoms. The fused ring system can be heterocyclic ring fused on aromatic group. Preferred heterocyclic rings include but are not limited to pyrrolylalkyl, tetrahydrofuryl, dihydrofuryl, tetrahydrothiophanyl, piperidyl, morpholine ring, hexamethylene ring, piperazinyl, and they can be substituted with following groups: $C_1$-$C_6$ alkyl, $C_1$-$C_6$ alkoxy, cyano, halogen, hydroxy, amino, nitro, mono($C_1$-$C_6$) alkylamino, di($C_1$-$C_6$) alkylamino, $C_2$-$C_6$ alkenyl, $C_2$-$C_6$ alkynyl, $C_1$-$C_6$ halogenated alkyl, $C_1$-$C_6$ halogenated alkoxy.

When applied to "in vivo", the term "effective amount" refers to a dose that can realize therapy, prophylaxis, alleviation and/or remission of the diseases or disorders of the present invention.

The term "subject" can refer to a patient or an animal, especially a mammal, such as human, dog, monkey, cattle, horse, etc., which accepts the composition of the present invention for therapy, prophylaxis, alleviation and/or remission of the diseases or disorders of the present invention.

The term "disease and/or disorder" refers to a physical state of the subject, in which the physical state relates to the diseases and/or disorders of the present invention.

SPECIFIC MODELS FOR CARRYING OUT THE INVENTION

Figure 1A:
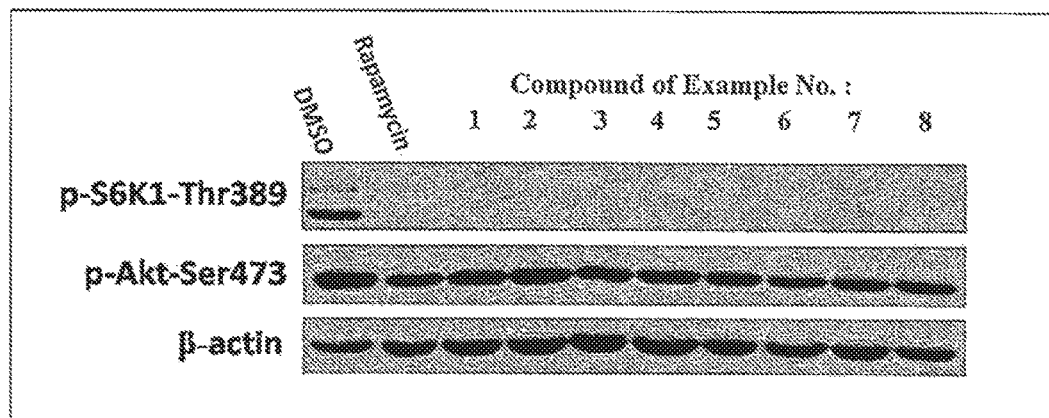
FIG. 1: Inhibition effects of compounds on phosphorylation of Thr389 of S6K1 and Ser473 of Aktin tumor cell A549; A, compounds of Examples No. 1-8; B, Compounds of Examples No. 9-17.

The embodiments of the present invention are illustrated in details in conjunction with examples. However, those skilled in the art would understand the following examples are merely to illustrate the present invention, rather than to limit the scope of the present invention. When specific conditions are not given in the examples, conventional conditions or conditions recommended by manufacturers are applied. The reagents or instruments which manufactures are not given are all conventional products commercially available in markets.

Melting points of compounds are measured by SRY-1 type melting point instrument, in which temperatures are not calibrated. 1H-NMR spectra are measured by VARIAN INOVA 600 type NMR spectrometer. Mass spectra are measured by API-150EX LC/MS high resolution magnetic mass spectrometer.

Example 1: Preparation of 31,42-O-carbonylmethyl-(4-methyl-thiazole bromide salt-3-yl-rapamycin (Compound 1)

Step 1: 1 g (1.09 mmol) of rapamycin was dissolved in 10 ml of dry dichloromethane, cooled to −10° C., then added with 0.87 g (1 mmol) of dry pyridine. To the reaction solution, 2.2 g (10 mmol) of bromoacetyl bromide in 5 ml of dichloromethane solution was slowly added dropwise, the addition was finished within 30 min, and the reaction was continued for 10 min then stopped. The reaction solution was adjusted to neutral pH with 1 mol/L hydrochloric acid, washed with distilled water 20 ml×3, then purified with column chromatography, to obtain 0.73 g of Intermediate 1 in form of white foam (n=1, $R_3$=Br, $R_4$=Br).

Step 2: 0.73 g (0.63 mmol) of Intermediate 1 (n=1, $R_3$=Br, $R_4$=Br) was dissolved in 20 ml of acetone, added with 0.94 g (9.45 mmol) of 4-methylthiazole, reacted at 60° C. for 5 h, the product was purified by column to obtain 0.7 g of Compound 1 in form of light yellow granules.

M.p. 142-145° C.; MS: 1193 [M-2Br-H]+, 597[(M-2Br)/2]+; 1H-NMR (600 MHz, DMSO-d6 δ ppm), 10.18 (d, 2H), 8.07 (s, 2H), 6.46 (s, 1H), 6.38 (m, 1H), 6.24 (m, 1H), 6.22 (m, 1H), 5.71 (s, 1H), 5.59 (s, 2H), 5.46 (m, 1H), 5.33 (s, 1H), 4.91 (m, 3H), 4.53 (s, 2H).

Example 2: Preparation of 42-O-carbonylmethyl-(4-methyl-thiazole bromide salt-3-yl)-rapamycin (Compound 2)

Step 1: 2 g (2.19 mmol) of rapamycin was dissolved in 25 ml of dry ethyl acetate, cooled to 0-5° C. To the reaction solution, 1.50 g (22 mmol) imidazole was added, 1.2 g (11 mmol) of trimethylchlorosilane in 5 ml of ethyl acetate solution was slowly added dropwise within 30 min, until the conversion to Intermediate 2 was completed. To the reaction solution, 10 ml of 0.5 mol/L $H_2SO_4$ solution was slowly added dropwise within 3 h, until the conversion of Intermediate 2 was completed, and then the product was purified with column chromatography, to obtain 1.3 g of Intermediate 3 in form of white foam.

Step 2: 1.3 g (1.3 mmol) of Intermediate 3 was dissolved in 15 ml of dichloromethane, cooled to −10° C., then added with 1.03 g (13 mmol) of dry pyridine. To the reaction solution, 1.31 g (6.5 mmol) of bromoacetyl bromide in 5 ml solution was slowly added dropwise, and the addition was completed within 30 min, the reaction was continued for 10 min then stopped. The reaction solution was adjusted to neutral pH with 1 mol/L hydrochloric acid, washed with distilled water 20 ml×3, then purified with column chromatography, to obtain 1.2 g of Intermediate 4 (n=1, $R_3$=Br, $R_4$=Br) in form of white foam.

Step 3: 1.2 g (1.1 mmol) of Intermediate 4 (n=1, $R_3$=Br, $R_4$=Br) was dissolved in 15 ml of acetone, added dropwise with 0.7 ml of 1 mol/L$H_2SO_4$ aqueous solution, the addition was completed within 1 h, the reaction was continued for 30 min, and the conversion of the reactant was completed. By column separation and purification, 1.05 g of Intermediate 5 (n=1, $R_3$=Br, $R_4$=Br) in form of white foam was obtained.

Step 4: 1.05 g (0.95 mmol) of Intermediate 5 (n=1, $R_3$=Br, $R_4$=Br) was dissolved in 20 ml of acetone, added with 0.94 g (9.5 mmol) of 4-methylthiazole, reacted at 60° C. for 5 h, the product was purified by column to obtain 1.02 g of Compound 2 in form of light yellow granules.

M.p. 130-133° C.; MS: 1053.8 [M-Br]+; 1H-NMR (600 MHz, DMSO-d6 δ ppm), 10.16 (d, 1H), 8.06 (s, 1H), 6.45 (s, 1H), 6.38 (m, 1H), 6.22 (m, 1H), 6.15 (m, 1H), 5.62 (s, 2H), 5.46 (M, 1H), 5.24 (s, 1H), 5.08 (d, 1H), 4.97 (s, 1H), 4.93 (s, 1H), 4.68 (m, 1H), 4.00 (s, 2H), 3.97 (s, 1H).

Example 3: Preparation of 31-O-carbonylmethyl-(4-methyl-thiazole bromide salt-3-yl)-rapamycin (Compound 3)

Step 1: 2 g (2 mmol) of Intermediate 3 was dissolved in 20 ml of ethyl acetate, cooled to 0-5° C. To the reaction solution, 1.36 g (20 mmol) of imidazole was added, 1.5 g (10 mmol) of tert-butyldimethylchlorosilane in 5 ml of ethyl acetate solution was slowly added dropwise with within 30 min, the reaction was continued for 30 min; by column separation, 1.3 g of Intermediate 6 was obtained. To the reaction solution, 0.5 ml of 0.5 mol/L$H_2SO_4$ solution was added within 30 min, and the addition was finished within 1 h, until the conversion of reactant was completed. By column separation and purification, 1.05 g of Intermediate 7 in form of white foam was obtained.

Step 2: 1.05 g (1.02 mmol) Intermediate 7 was dissolved in 10 ml of dichlormethane, cooled to −10° C., then added with 0.81 g (10.2 mmol) of dry pyridine. To the reaction solution, 1.03 g (5.1 mmol) of bromoacetyl bromide in 5 ml solution was slowly added dropwise, the addition was completed within 30 min. The reaction was continued for 10 min and then stopped. The reaction solution was adjusted to neutral pH with 1 mol/L hydrochloric acid, washed with distilled water 20 ml×3, then purification was carried out by using column chromatography method, to obtain 0.73 g of Intermediate 8 (n=1, $R_3$=Br, $R_4$=Br) in form of white foam.

Step 3: 0.73 g (0.64 mmol) of Intermediate 8 (n=1, $R_3$=Br, $R_4$=Br) was dissolved in 10 ml of acetone, added dropwise with 0.5 ml of 2 mol/L $H_2SO_4$ solution, the addition was completed within 30 min, the reaction was continued for 30 min, until the conversion of reactant was completed. By column separation and purification, 0.4 g of Intermediate 9 (n=1, $R_3$=Br, $R_4$=Br) in form of white foam was obtained.

Step 4: 0.4 g (0.39 mmol) of Intermediate 9 (n=1, $R_3$=Br, $R_4$=Br) was dissolved in 20 ml of acetone, added with 0.38 g (3.90 mmol) of 4-methylthiazole, reacted at 60° C. for 5 h; by column separation, 0.27 g (0.24 mmol) of Compound 3 in form of light yellow granules was obtained.

M.p. 130-132° C.; MS: 1054 [M-Br]+; 1H-NMR (600 MHz, DMSO-d6 δ ppm), 10.16 (d, 1H), 8.05 (s, 1H), 6.45 (s, 1H), 6.37 (m, 1H), 6.25 (m, 1H), 6.18 (m, 2H), 5.70 (s, 2H), 5.46 (m, 1H), 5.35 (s, 1H), 4.55 (d, 2H), 4.04 (s, 1H).

Example 4: Preparation of 31,42-O-carbonylmethyl-(4,5-dimethyl-thiazole bromide salt-3-yl)-rapamycin (Compound 4)

Preparation method was referred to Example 1 (n=1, $R_3$=Br, $R_4$=Br, $R_5$=4, 5-dimethylthiazole).

m.p. 135-139° C.; MS: 1220.9 [M-2Br-H]+; 1H-NMR (600 MHz, DMSO-d6 δ ppm), 10.03 (d, 2H), 6.46 (s, 1H), 6.37 (m, 1H), 6.24 (m, 1H), 6.18 (m, 1H), 6.12 (m, 1H), 5.76 (m, 3H), 5.62 (s, 2H), 5.46 (m, 1H), 5.32 (s, 1H), 5.32 (s, 1H), 4.93 (s, 1H), 4.83 (m, 2H), 4.61 (s, 1H), 4.55 (s, 1H), 4.52 (s, 1H).

Example 5: Preparation of 42-O-carbonylmethyl-(4,5-dimethyl-thiazole bromide salt-3-yl)-rapamycin (Compound 5)

Preparation method was referred to Example 2 (n=1, $R_3$=Br, $R_4$=Br, $R_3$=4, 5-dimethylthiazole).

m.p. 135-138° C.; MS: 1067.9 [M-Br]+; 1H-NMR (600 MHz, DMSO-d6 δ ppm), 10.03 (d, 1H), 6.49 (s, 1H), 6.37 (m, 1H), 6.21 (m, 1H), 6.14 (m, 2H), 5.62 (m, 2H), 5.46 (m, 1H), 5.23 (s, 1H), 5.08 (s, 1H), 4.97 (s, 1H), 4.93 (s, 1H), 4.68 (s, 1H), 4.06 (s, 2H), 4.01 (s, 1H).

Example 6: Preparation of 31-O-carbonylethyl-(4,5-dimethyl-thiazole bromide salt-3-yl)-rapamycin (Compound 6)

Preparation method was referred to Example 3 (n=1, $R_3$=Br, $R_4$=Br, $R_5$=4, 5-dimethylthiazole).

m.p. 125-127° C.; MS: 1067.7 [M-Br]+; 1H-NMR (600 MHz, DMSO-d6 δ ppm), 10.02 (d, 1H), 6.45 (s, 1H), 6.37 (m, 1H), 6.25 (m, 1H), 6.20 (m, 1H), 6.15 (m, 1H), 5.70 (m, 2H), 5.45 (m, 1H), 5.33 (s, 1H), 5.08 (s, 1H), 4.93 (s, 1H), 4.81 (m, 1H), 4.56 (m, 3H), 4.03 (m, 1H).

Example 7: Preparation of 31,42-O-carbonylmethyl-(pyridine bromide salt-1-yl)-rapamycin (Compound 7)

Preparation method was referred to Example 1 (n=1, $R_3$=Br, $R_4$=Br, $R_5$=pyridine).

m.p. 140-142° C.; MS: 1153 [M-Br]+; 1H-NMR (600 MHz, DMSO-d6 δ ppm), 8.96 (d, 4H), 8.72 (m, 2H), 8.22 (m, 4H), 6.44 (s, 1H), 6.40 (m, 1H), 6.24 (m, 1H), 6.17 (m, 2H), 5.87 (m, 1H), 5.79 (m, 1H), 5.48 (m, 1H), 5.29 (s, 1H), 4.95 (m, 2H), 4.81 (s, 1H), 4.52 (m, 3H).

Example 8: Preparation of 31, 42-O-carbonylmethyl-(3-hydroxy-pyridine bromide salt-1-yl)-rapamycin (Compound 8)

Synthesis method was referred to Example 1 (n=1, $R_3$=Br, $R_4$=Br, $R_5$=3-hydroxypyridine).

m.p. 120-124° C.; MS; 1185.4 [M-2Br-H]+; 1H-NMR (600 MHz, DMSO-d6 δ ppm), 12.04 (s, 2H), 8.60 (m, 4H), 8.00 (m, 4H), 6.43 (m, 2H), 6.12 (m, 3H), 5.61 (m, 3H), 5.56 (m, 1H).

Example 9: Preparation of 31,42-O-carbonylmethyl-(3-methyl-pyridine bromide salt-1-yl)-rapamycin (Compound 9)

Preparation method was referred to Example 1 (n=1, $R_3$=Br, $R_4$=Br, $R_5$=3-methylpyridine).

m.p. 159-162° C.; MS: 1181.2 [M-2Br-H]+; 1H-NMR (600 MHz, DMSO-d6 δ ppm), 9.00 (s, 1H), 8.89 (m, 2H), 8.81 (m, 1H), 8.57 (s, 2H), 8.14 (m, 2H), 6.46 (s, 1H), 6.38 (m, 1H), 6.23 (m, 1H), 6.14 (m, 2H), 5.80 (m, 5H), 5.46 (m, 1H), 5.29 (m, 1H).

Example 10: Preparation of 42-O-carbonylmethyl-(pyridine bromide salt-1-yl)-rapamycin (Compound 10)

Preparation method was referred to Example 2 (n=1, $R_3$=Br, $R_4$=Br, $R_5$=pyridine).

m.p. 135-137° C.; MS: 1034.1 [M-Br]+; 1H-NMR (600 MHz, DMSO-d6 δ ppm), 9.07 (d, 1H), 9.02 (m, 1H), 8.71 (m, 1H), 8.24 (m, 2H), 8.14 (m, 2H), 6.45 (s, 1H), 6.41 (m, 1H), 6.22 (m, 1H), 6.14 (m, 1H), 5.80 (m, 5H), 5.67 (m, 2H), 5.44 (m, 1H), 5.25 (s, 1H), 5.08 (m, 1H).

Example 11: Preparation of 42-O-carbonylmethyl-(3-methyl-pyridine bromide salt-1-yl)-rapamycin (Compound 11)

Preparation method was referred to Example 2 (n=1, $R_3$=Br, $R_4$=Br, $R_5$=3-methylpyridine).

m.p. 138-140° C.; MS: 1048 [M-Br]+; 1H-NMR (600 MHz, DMSO-d6 δ ppm), 9.07 (d, 1H), 9.02 (m, 1H), 8.71 (m, 1H), 8.24 (m, 2H), 8.14 (m, 2H), 6.45 (s, 1H), 6.41 (m, 1H), 6.22 (m, 1H), 6.14 (m, 1H), 5.80 (m, 5H), 5.67 (m, 2H), 5.44 (m, 1H), 5.25 (s, 1H), 5.08 (m, 1H).

Example 12: Preparation of 42-O-carbonylmethyl-(3-hydroxy-pyridine bromide salt-1-yl)-rapamycin (Compound 12)

Preparation method was referred to Example 2 (n=1, $R_3$=Br, $R_4$=Br, $R_5$=3-hydroxypyridine).

m.p. 146-148° C.; MS: 1050 [M-Br]+; 1H-NMR (600 MHz, DMSO-d6 δ ppm), 12.08 (s, 1H), 8.60 (m, 1H), 8.53 (m, 1H), 8.02 (m, 2H), 6.45 (m, 2H), 6.38 (s, 1H), 6.22 (m, 1H), 6.12 (m, 2H), 5.60 (m, 2H), 5.48 (m, 1H), 5.25 (m, 1H), 5.08 (m, 1H).

Example 13: Preparation of 42-O-carbonylmethyl-(4-methyl-pyridine bromide salt-1-yl)-rapamycin (Compound 13)

Preparation method was referred to Example 2 (n=1, $R_3$=Br, $R_4$=Br, $R_5$=4-methylpyridine).
m.p. 157-160° C.; MS: 1048.1 [M-Br]+; 1H-NMR (600 MHz, DMSO-d6 δ ppm), 8.89 (d, 1H), 8.05 (m, 2H), 6.45 (s, 1H), 6.41 (m, 1H), 6.22 (m, 1H), 6.12 (m, 2H), 5.61 (m, 3H), 5.46 (m, 1H), 5.25 (m, 1H), 5.08 (d, 1H), 4.93 (m, 2H).

Example 14: Preparation of 31,42-O-carbonylmethyl-(4-methyl-pyridine bromide salt-1-yl)-rapamycin (Compound 14)

Preparation method was referred to Example 1 (n=1, $R_3$=Br, $R_4$=Br, $R_5$=4-methylpyridine).
m.p. 181-183° C.; MS: 1181.2 [M-2Br-H]+; 1H-NMR (600 MHz, DMSO-d6 δ ppm), 8.90 (d, 2H), 8.78 (d, 2H), 8.06 (m, 4H), 6.46 (d, 1H), 6.38 (m, 1H), 6.20 (m, 1H), 6.14 (m, 2H), 5.80 (d, 1H), 5.62 (m, 4H), 5.47 (m, 1H), 5.29 (s, 1H).

Example 15: Preparation of 31-O-carbonylmethyl-(3-methyl-pyridine bromide salt-1-yl)-rapamycin (Compound 15)

Preparation method was referred to Example 3 (n=1, $R_3$=Br, $R_4$=Br, $R_5$=3-methylpyridine).

m.p. 138-140° C.; MS: 1048.1 [M-Br]+; 1H-NMR (600 MHz, DMSO-d6 δ ppm), 8.88 (d, 1H), 8.80 (d, 1H), 8.57 (m, 1H), 8.12 (m, 1H), 6.45 (m, 1H), 6.40 (m, 1H), 6.23 (m, 1H), 6.17 (m, 2H), 5.81 (d, 1H), 5.74 (m, 2H), 5.47 (m, 1H) 5.28 (s, 1H).

Example 16: Preparation of 31-O-carbonylmethyl-(pyridine bromide salt-1-yl)-rapamycin (Compound 16)

Preparation method was referred to Example 3 (n=1, $R_3$=Br, $R_4$=Br, $R_5$=pyridine).
m.p. 140-142° C.; MS: 1034 [M-Br]+; 1H-NMR (600 MHz, DMSO-d6 δ ppm), 8.96 (d, 2H), 8.72 (m, 1H), 8.22 (m, 2H), 6.44 (s, 1H), 6.40 (m, 1H), 6.24 (m, 1H), 6.17 (m, 2H), 5.87 (m, 1H), 5.79 (m, 1H), 5.48 (m, 1H), 5.29 (s, 1H), 4.95 (m, 2H), 4.81 (s, 1H), 4.52 (m, 3H).

Example 17: Preparation of 31-O-carbonylmethyl-(4-methyl-pyridine bromide salt-1-yl)-rapamycin (Compound 17)

Preparation method was referred to Example 3 (n=1, $R_3$=Br, $R_4$=Br, $R_5$=4-methylpyridine).
m.p. 145-148° C.; MS: 1048.1 [M-Br]+; 1H-NMR (600 MHz, DMSO-d6 δ ppm), 8.77 (d, 2H), 8.03 (d, 2H), 6.44 (s, 1H), 6.40 (m, 1H), 6.23 (m, 1H), 6.16 (m, 2H), 5.80 (d, 1H), 5.70 (d, 1H), 5.44 (m, 1H), 5.29 (m, 1H), 5.29 (s, 1H).

Example 18: Solubility Test

The Compounds 1-17 of the present invention were taken, and separately tested according to the Solubility Test Method of the Part II of Chinese Pharmacopoeia, 2010 Edition. The results are shown in Table 2:

TABLE 2

Water solubility of Compounds 1-17

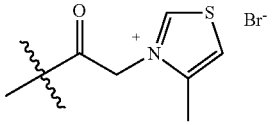

| Compound No. | $R_1$ | $R_2$ | Water solubility (mg/ml) | Comparison to water solubility of rapamycin |
|---|---|---|---|---|
| Rapamycin | H | H | 0.0026 | 1 |
| 1 | 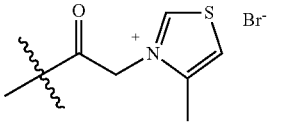 | | 34.5 | 13269 |

TABLE 2-continued

Water solubility of Compounds 1-17

| Compound No. | R₁ | R₂ | Water solubility (mg/ml) | Comparison to water solubility of rapamycin |
|---|---|---|---|---|
| 2 | [4-methylthiazolium-CH₂-C(O)-, Br⁻] | H | 0.028 | 11 |
| 3 | H | [4-methylthiazolium-CH₂-C(O)-, Br⁻] | 10 | 3846 |
| 4 | [4,5-dimethylthiazolium-CH₂-C(O)-, Br⁻] | [4,5-dimethylthiazolium-CH₂-C(O)-, Br⁻] | 100 | 38462 |
| 5 | [4,5-dimethylthiazolium-CH₂-C(O)-, Br⁻] | H | 4.2 | 1615 |
| 6 | H | [4,5-dimethylthiazolium-CH₂-C(O)-, Br⁻] | 23.3 | 8962 |
| 7 | [pyridinium-CH₂-C(O)-, Br⁻] | [pyridinium-CH₂-C(O)-, Br⁻] | 85 | 32692 |
| 8 | [3-hydroxypyridinium-CH₂-C(O)-, Br⁻] | [3-hydroxypyridinium-CH₂-C(O)-, Br⁻] | 0.1 | 38 |

TABLE 2-continued

Water solubility of Compounds 1-17

[Structure of rapamycin analog with OR₁ and OR₂ substituents shown]

| Compound No. | R₁ | R₂ | Water solubility (mg/ml) | Comparison to water solubility of rapamycin |
|---|---|---|---|---|
| 9 | -C(O)-CH₂-N⁺(3-methylpyridinium) Br⁻ | -C(O)-CH₂-N⁺(3-methylpyridinium) Br⁻ | 47 | 18077 |
| 10 | -C(O)-CH₂-N⁺(pyridinium) Br⁻ | H | 0.025 | 10 |
| 11 | -C(O)-CH₂-N⁺(3-methylpyridinium) Br⁻ | H | 6.7 | 2577 |
| 12 | -C(O)-CH₂-N⁺(3-hydroxypyridinium) Br⁻ | H | 0.01 | 4 |
| 13 | -C(O)-CH₂-N⁺(4-methylpyridinium) Br⁻ | H | 6 | 2308 |
| 14 | -C(O)-CH₂-N⁺(4-methylpyridinium) Br⁻ | -C(O)-CH₂-N⁺(4-methylpyridinium) Br⁻ | 120 | 46154 |
| 15 | H | -C(O)-CH₂-N⁺(3-methylpyridinium) Br⁻ | 26.7 | 10269 |

TABLE 2-continued

Water solubility of Compounds 1-17

| Compound No. | $R_1$ | $R_2$ | Water solubility (mg/ml) | Comparison to water solubility of rapamycin |
|---|---|---|---|---|
| 16 | H | [CH2-C(=O)-CH2-N+(pyridinium) Br−] | 52.6 | 20231 |
| 17 | H | [CH2-C(=O)-CH2-N+(4-methylpyridinium) Br−] | 62.5 | 24038 |

It can be seen from data of Table 2 that the compounds of the present invention have water solubility significantly higher than that of rapamycin, and even by 3 to 4 orders of magnitudes for some of these compounds.

Example 19: Experimental Evaluation of Toxicity on Rat Primary Hepatocytes

Experimental method: Liver lobes of SD rat were placed in sterilized plate, added with a suitable amount of liver cell cleaning solution (precooled at 4° C.), the liver was shredded and fibrous connective tissues were removed to form a liver cell suspension, screened with 200 mesh screen and placed in 50 ml centrifuge tube, centrifuged at 500 rpm for 1-2 min; the supernatant was removed, the precipitate was added with 20-30 ml of RPMI 1.640 (precooled at 4° C.) and washed 3 times; isovolumetric liver cell suspension was taken and suspended in Percoll separating solution I, mixed by turning upside down, centrifuged at 4° C. and 800 rpm for 10 min, the supernatant was discarded, the liver cells were washed with PBS once (800 rpm, 5 min). The liver cell precipitate was added into liver cell culture fluid, resuspended and diluted to 10 ml, and a suitable amount thereof was taken for counting and survival rate was determined by using 0.4% trypan blue. The liver cells with survival rate of 90% or more were inoculated in a density of $2 \times 10^3$ on 96-well plate, 100 μl of RPMI 1640 culture medium was added to each well, culture was performed at 37° C., 5% $CO_2$ for 24 h. The compounds were diluted with DMSO to desired concentrations and added to each well in an amount of 1 μl (final compound concentrations were usually initiated from 1000 μM, 10× gradient dilution, 6 gradients), and blank control was added with 1 μl of DMSO.

After the cells were cultured at 37° C., 5% $CO_2$ for 24 h, 100 μl of ATP detection reagent was added, incubated under shock for 15 min. fluorescence values of wells were read by ELIASA. Cell survival rates for each example compounds were calculated, and then GIs values (concentrations of added compounds at which growth of 50% cells was inhibited) were calculated. The results were shown in Table 4. Obviously, the toxicities of the compounds were significantly less than that of rapamycin.

TABLE 4

$GI_{50}$ values of some example compounds on rat primary hepatocytes

| Compound | $GI_{50}$ (μM) |
|---|---|
| Rapamycin | 24.822 |
| Compound of Example 11 | 71.753 |
| Compound of Example 13 | 44.936 |
| Compound of Example 17 | 54.311 |

The data of Table 4 show that the compounds of the present invention have toxicities significantly less than rapamycin.

Example 20: Experiment of Inhibition Activities of the Compounds to mTORC1 and mTORC2

Molecular mechanism of action of the example compounds in tumor cell A549.

Experimental materials: DMEM high-glucose cell culture media (Hyclone Company), fetal calf serum (FBS) (Gibco Company), penicillin and streptomycin were purchased from North China Pharmaceutical Co., Ltd, phosphate buffer saline (PBS) was purchased from Gibco Company, pancreatic enzyme and dimethylsulfoxide (DMSO) were products of Sigma Company. A549 cell line (human lung adenocarcinoma cell line) was purchased from ATCC. Mouse anti-human p-p70S6K(T389) monoclonal antibody was purchased from Cell Signaling Technology Company, mouse anti-human p70S6K monoclonal antibody was purchased from Cell Signaling Technology Company, mouse anti-human p-AKT (S473) monoclonal antibody was purchased from Cell Signaling Technology Company, mouse anti-human AKT monoclonal antibody was purchased from Cell Signaling Technology Company. Horseradish peroxidase-labeled goat anti-mouse, goat anti-mouse monoclonal antibodies were purchased from Cell Signaling Technology Company. Cell lysis solution was purchased from Beijing Solarbio Science and Technology Co., Ltd., loading buffer was purchased from Biyuntian Company, SDS electrophoretic buffer solution was purchased from Biyuntian Company, Towbin transfer buffer was purchased from Biyuntian Company, TBS was purchased from Biyuntian Company, TBST was purchased from Biyuntian Company. ECL chemiluminescence solution was purchased from Beijing Pulilai Genetic Technology Co., Ltd., developing solution and fixing solution were purchased from the Tenth Chemical Plant of Shijiazhuang, N.C. membrane was purchased from Whatman Company, photographic film was purchased from Carestream (Xiamen) Medical Equipment Co., Ltd., skimmed milk powder was purchased from Beijing Xikai Creative Technology Co., Ltd.

Experimental Method

Figure 1B:
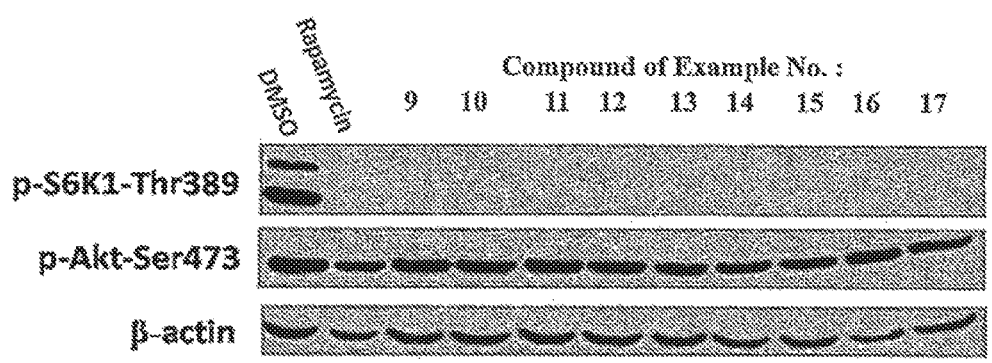

A549 cells were spread on a 96-well plate, the cells grew to density of 80%-90% and then cultured overnight under serum deprivation condition, co-incubated on the second day with 167 nM insulin and the compounds for 2 hours, then the cells were lysed and the phosphorylation levels for the example compounds at Thr389 site of S6K1 (corresponding to mTORC1) and Ser473 site of Akt (corresponding to mTORC2) were detected by Western Blot method, and which were used to semi-quantitatively reflect the inhibition levels of the compounds to mTORC1 and mTORC2 (in the bands of the results, absence of blot represented expression of corresponding protein was inhibited, while presence of blot represented the expression was not inhibited). Positive control compound was Rapamycin. The results of evaluation are shown in FIG. 1 (FIG. 1A and FIG. 1B). Specific steps were as follows:

1. Treatment of Cells:
   1) the cells were inoculated on 6-well plate, and the cells spread 80%-90% after 24 h;
   2) the cells were washed with PBS once, then 2 mL serum-free culture media was used for replacement and the culture was performed overnight under serum deprivation condition;
   3) to the treated cells, 2 μL of cell culture fluid containing the compound to be tested (20 μM) and insulin (167 nM) was added and co-incubation was performed for 2 h.

2. Lysis of Cells:
   1) the cells on the 6-well plate were washed off with 10 ml PBS, centrifuged at 1500 rpm for 5 min;
   2) the supernatant was discarded then 60 μl cell lysis buffer (containing protease inhibitor) was added, the cells were lysed on ice for 20-30 min, after 10 min, oscillated with oscillator for 2-3 s, and put back on ice;
   3) oscillation was performed again for 3 s before centrifugation, then centrifuged at 4° C., 13000 rpm, for 10 min;
   4) 2×loading buffer 60 μl was added, subjected to boiling water bath for 5 min, and cryopreservated at −20° C. or −80° C. for standby use;

3. Western Blotting Analysis:
   1) SDS-PAGE, 80 V voltage was firstly used for running to spacer gel, then 120 V voltage was used for running separation gel;
   2) transfer, wet transfer, in ice-bath, 250 mA, 150 min;
   3) 5% milk was used for sealing at room temperature for 1-2 h (or overnight at 4° C.);
   4) primary antibody was added (diluted with TBS), stood overnight at 4° C.;
   5) TBST washing 3×10 min.
   6) secondary antibody was added (1:2000 diluted with 3% skimmed milk powder in TBS), incubation was performed at room temperature at sealing film for 2 hours;
   7) TBST washing 3×10 min.
   8) ECL chemiluminescence developing solutions A, B, each in 500 μl, were mixed in a plate dish, and washed for 5 min;
   9) the film was placed in exposure clamp, exposed in darkroom for a certain time, then placed in developing solution for 2 min, in fixing solution for 5 min, the film was washed with tap water, and dried by baking;
   10) pictures were taken and kept.

The results showed that the compounds of the present invention could effectively inhibit mTORC1, and their inhibition effects are not inferior to rapamycin (rapamycin could only inhibit mTORC1, so that our compounds had activities not inferior to rapamycin).

Example 21: Experiment of Tumor Cell Inhibition

The activities of example compounds to tumor cell A549 were evaluated.

Experimental materials: DMEM high-glucose cell culture media (Hyclone Company), fetal calf serum (FBS) (Gibco Company), penicillin and streptomycin were purchased from North China Pharmaceutical Co., Ltd, phosphate buffer saline (PBS) was purchased from Gibco Company, Cell Titer-Glo® cell viability detection reagent was purchased from Promega Company, pancreatin and dimethylsulfoxide (DMSO) were products of Sigma Company. A549 cell line (human lung adenocarcinoma cell line) was purchased from ATCC.

Experimental Method

The cells were inoculated on a 96-well plate with white wall and penetrative bottom (Costar) in amount of 5000 cells per well, cultured at condition of 37° C., 5% $CO_2$ for 24 h. The compounds to be tested were dissolved with DMSO and diluted to 100 mM, to obtain mother liquids of the compounds.

DMEM culture solution containing 2% FBS was used to diluted the compounds, in which concentration gradients were 3, and concentration range was 100 μM to 3 nM. The compounds in various dilution degrees were added to the cultured cells on the 96-well plate, 100 μl per well. Culture was performed at 37° C., CO$_2$ for 72 h, supernatant was discarded, and cell viability detection test was performed.

AfterCell Titer-Glo® reaction buffer solution was mixed with isometric substrate, the mixture was added to 96-well plate, 100 μl per well. Cell lysis was induced by horizontally shaking for 4 min. Reaction signal was stabilized by balancing at room temperature for 15 min. Chemiluminescence units in each well of the 96-well plate were detected by using chemiluminescence detector.

Inhibition rates at different dilution degrees of each compound were calculated according to chemiluminescence value of each well, and Origin 8.0 software was used for S-type curve fitting of each compound, and for calculating EC$_{50}$ value. The results were shown in Table 5.

TABLE 5

EC$_{50}$ values of concentration of some example compounds for tumor cell A549

| Compound | IC$_{50}$ (μM) |
| --- | --- |
| rapamycin | 49.35 |
| Compound of Example 1 | 17.39 |
| Compound of Example 2 | 19.31 |
| Compound of Example 3 | 3.04 |
| Compound of Example 4 | 6.23 |
| Compound of Example 5 | 7.40 |
| Compound of Example 6 | 52.26 |
| Compound of Example 7 | 46.68 |
| Compound of Example 8 | 45.98 |
| Compound of Example 9 | 25.12 |
| Compound of Example 10 | 66.32 |
| Compound of Example 11 | 52.80 |
| Compound of Example 12 | 51.48 |
| Compound of Example 13 | 44.80 |
| Compound of Example 14 | 44.0 |
| Compound of Example 15 | 52.70 |
| Compound of Example 16 | 57.71 |
| Compound of Example 17 | 40.80 |

The results showed that the compound of the present invention could effectively inhibit tumor cells, and some compounds had effects even superior to rapamycin, and thus are promising in the manufacture of anti-tumor drugs.

Example 22: Experiment of Inhibition to Drug-Resistant Tumor Cell Line

The activity of example compounds to multi-drug resistant tumor cell line MES-SA was evaluated.

Experimental materials: DMEM high-glucose cell culture media (Hyclone Company), fetal calf serum (FBS) (Gibco Company), penicillin and streptomycin were purchased from North China Pharmaceutical Co., Ltd, phosphate buffer saline (PBS) was purchased from Gibco Company, Cell Titer-Glo® cell viability detection reagent was purchased from Promega Company, pancreatin and dimethylsulfoxide (DMSO) were products of Sigma Company. MES-SA cell line (human uterine sarcoma cell line) was purchased from ATCC. MRC5 cell (human embryonic lung fibroblast) was purchased from ATCC.

Experimental Method

The cells were inoculated on a 96-well plate with white wall and penetrative bottom (Costar) in amount of 5000 cells per well, cultured at condition of 37° C., 5% CO$_2$ for 24 h. The compounds to be tested were dissolved with DMSO and diluted to 100 mM, to obtain mother liquids of the compounds.

DMEM culture solution containing 2% FBS was used to diluted the compounds, in which concentration gradients were 3, and concentration range was 100 μM to 0.046 μM. The compounds in various dilution degrees were added to the cultured cells on the 96-well plate, 100 μl per well. Culture was performed at 37° C., CO$_2$ for 72 h, supernatant was discarded, and cell viability detection test was performed.

AfterCell Titer-Glo® reaction buffer solution was mixed with isometric substrate, the mixture was added to 96-well plate, 100 μl per well. Cell lysis was induced by horizontally shaking for 4 min. Reaction signal was stabilized by balancing at room temperature for 15 min. Chemiluminescence units in each well of the 96-well plate were detected by using chemiluminescence detector.

Inhibition rates at different dilution degrees of each compound were calculated according to chemiluminescence value of each well, and Origin 8.0 software was used for S-type curve fitting of each compound, and for calculating EC$_{50}$ value. The ratio of EC$_{50}$ value of compound for MRC5 cell to EC$_{50}$ value of compound for MES-SA cell was used as therapeutic index for the compound. The experimental results were shown in Table 6.

TABLE 6

EC$_{50}$ values and therapeutic indexes of some example compounds for tumor cell MES-SA

| Compound | IC$_{50}$ (μM) | Therapeutic index |
| --- | --- | --- |
| rapamycin | <0.046 | >635.09 |
| Compound of Example 1 | <0.046 | >259.8 |
| Compound of Example 2 | <0.046 | >1811.9 |
| Compound of Example 3 | <0.046 | >1501.1 |
| Compound of Example 4 | <0.046 | >787.2 |
| Compound of Example 5 | <0.046 | >1371.1 |
| Compound of Example 6 | <0.046 | >455.1 |
| Compound of Example 7 | <0.046 | >442.7 |
| Compound of Example 8 | <0.046 | >1441.6 |
| Compound of Example 9 | 7.21 | 12.1 |
| Compound of Example 10 | 10.93 | 3.4 |
| Compound of Example 11 | <0.046 | >1888.7 |
| Compound of Example 12 | <0.046 | >146.5 |
| Compound of Example 13 | <0.046 | >1559.0 |
| Compound of Example 14 | <0.046 | >2136.8 |
| Compound of Example 15 | <0.046 | >331.5 |
| Compound of Example 16 | <0.046 | >364.8 |
| Compound of Example 17 | <0.046 | >317.7 |

The results showed that the compounds of the present invention could effectively inhibit proliferation of multi-drug resistant tumor cell line MES-SA, and their inhibition activities to normal cells were generally lower than their inhibition activities to MES-SA, so that they had good therapeutic indexes and good safety. Some compounds had effects superior to rapamycin, and were promising for making or acting as anti-tumor drugs.

Although specific models for carrying out the invention were described in details, those skilled in the art would understand that these details can be modified and changed according to the teachings of disclosures, and all these changes fall into the protection scope of the present invention. The whole protection scope of the present invention is given by the appended claims and any equivalents thereof.

What is claimed is:
1. A compound of Formula I, or a pharmaceutically acceptable salt or hydrate thereof:

Formula I

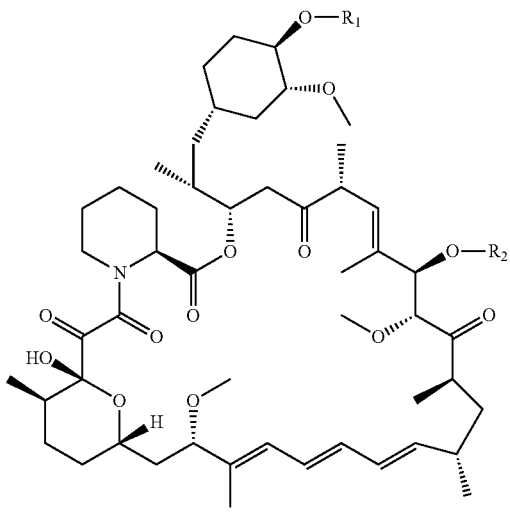

wherein,
$R_1$ and $R_2$ are independently selected from H, A and B, and $R_1$, $R_2$ cannot be H simultaneously; and at least one of $R_1$ and $R_2$ is Formula A;

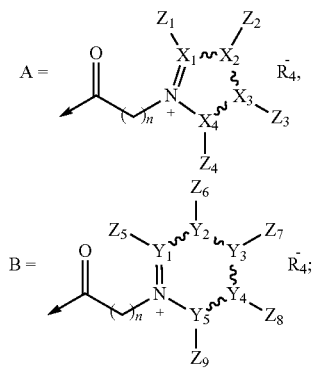

wherein, in Formula A or Formula B,
arrows refer to sites where A or B links to mother ring of Formula I;
n independently is 1, 2, 3, 4, 5, 6 or 7;
$R_4$ is independently selected from fluorine, chlorine, bromine, iodine, nitro, and cyano;
$X_1$, $X_2$, $X_3$, $X_4$, $Y_1$, $Y_2$, $Y_3$, $Y_4$, and $Y_5$ are independently selected from C, S, O, N and Se atoms;
$X_1$~$X_2$, $X_2$~$X_3$, $X_3$~$X_4$, $Y_1$~$Y_2$, $Y_2$~$Y_3$, $Y_3$~$Y_4$, $Y_4$~$Y_5$ are independently single bond or double bond;
$Z_1$, $Z_2$, $Z_3$, $Z_4$, $Z_5$, $Z_6$, $Z_7$, $Z_8$, $Z_9$ are independently selected from hydrogen atom, hydroxy, aldehyde group, carboxyl, amino, cyano, halogen, $C_1$-$C_6$ alkyl, $C_3$-$C_{10}$ cycloalkyl, $C_1$-$C_6$ alkoxy, $C_1$-$C_6$ alkylthiol, $C_3$-$C_{10}$ cycloalkoxy, $C_1$-$C_6$ alkenyl, eneynylheterocyclic ring, heterocycloalkyl, substituted heterocycloalkyl, aromatic ring, aromatic heterocyclic ring, benzo-aromatic heterocyclic ring, wherein the $C_1$-$C_6$ alkyl, aromatic ring, aromatic heterocyclic ring, benzo-aromatic heterocyclic ring are not substituted or substituted with 1, 2, 3, 4 or 5 substituents independently selected from the following groups: —F, —Cl, —Br, —I, nitro, hydroxy, amino, cyano, $C_1$-$C_6$ alkylthiol, $C_1$-$C_6$ alkyl, $C_1$-$C_6$ alkenyl, $C_1$-$C_6$ alkynyl and $C_1$-$C_6$ alkoxy;
wherein in Formula A, N atom together with $X_1$, $X_2$, $X_3$, $X_4$ form a thiazole ring.

2. The compound of Formula I, or a pharmaceutically acceptable salt or hydrate thereof according to claim 1, wherein:
$R_1$ and $R_2$ are independently selected from H, carbonylmethyl-(4-methyl-thiazole $R_4$ salt-3-yl), carbonylmethyl-(4, 5-dimethyl-thiazole $R_4$ salt-3-yl), carbonylmethyl-(pyridine $R_4$ salt-1-yl), carbonylmethyl-(3-hydroxy-pyridine $R_4$ salt-1-yl), carbonylmethyl-(3-methyl-pyridine $R_4$ salt-1-yl) and carbonylmethyl-(4-methyl-pyridine $R_4$ salt-1-yl), wherein $R_4$ is independently selected from fluorine, chlorine, bromine, iodine, nitro and cyano; and $R_1$, $R_2$ cannot be H simultaneously.

3. The compound of Formula I, or a pharmaceutically acceptable salt or hydrate thereof according to claim 1, wherein the compound is selected from the following compounds:
31,42-bis-O-carbonylmethyl-(4-methyl-thiazole bromide salt-3-yl)-rapamycin,
42-O-carbonylmethyl-(4-methyl-thiazole bromide salt-3-yl)-rapamycin,
31-O-carbonylmethyl-(4-methyl-thiazole bromide salt-3-yl)-rapamycin,
31,42-bis-O-carbonylmethyl-(4,5-dimethyl-thiazole bromide salt-3-yl)-rapamycin,
42-O-carbonylmethyl-(4,5-dimethyl-thiazole bromide salt-3-yl)-rapamycin, and
31-O-carbonylmethyl-(4,5-dimethyl-thiazole bromide salt-3-yl)-rapamycin.

4. A pharmaceutical composition, which comprises the compound or a pharmaceutically acceptable salt or hydrate thereof of claim 1.

5. A coronary stent, comprising a drug coating comprising the compound or a pharmaceutically acceptable salt or hydrate thereof according to claim 1.

6. A method for inhibiting mTOR, inhibiting mTORC1 or inhibiting PI3K-Akt-mTOR signal pathway, comprising a step of administering to a subject or a cell in need thereof an effective amount of the compound or a pharmaceutically acceptable salt or hydrate thereof according to claim 1.

7. A method for treatment of kidney cancer, lymphoma, lung cancer, liver cancer, breast cancer, neuroendocrine cancer, uterine sarcoma or gastric cancer, comprising a step of administering to a subject in need thereof, an effective amount of the compound or a pharmaceutically acceptable salt or hydrate thereof according to claim 1.

8. The compound of Formula I, or a pharmaceutically acceptable salt or hydrate thereof according to claim 1, wherein in Formula B, N atom together with $Y_1$, $Y_2$, $Y_3$, $Y_4$, $Y_5$ form a pyridine ring.

9. The compound of Formula I, or a pharmaceutically acceptable salt or hydrate thereof according to claim 1, wherein $Z_1$, $Z_2$, $Z_3$, $Z_4$, $Z_5$, $Z_6$, $Z_7$, $Z_8$, $Z_9$ are independently selected from hydrogen atom, hydroxy, and methyl.

10. The compound of Formula I, or a pharmaceutically acceptable salt or hydrate thereof according to claim 1, wherein $R_1$ and $R_2$ are independently selected from H, carbonylmethyl-(4-methyl-thiazole bromide salt-3-yl), carbonylmethyl-(4, 5-dimethyl-thiazole bromide salt-3-yl), carbonylmethyl-(pyridine bromide salt-1-yl), carbonylmethyl-(3-hydroxy-pyridine bromide salt-1-yl), carbonylmethyl-(3-methyl-pyridine bromide salt-1-yl) and carbonylmethyl-(4-methyl-pyridine bromide salt-1-yl), and $R_1$, $R_2$ are not H simultaneously.

11. The pharmaceutical composition of claim 4 further comprising a pharmaceutically acceptable excipient.

12. The compound of Formula I, or a pharmaceutically acceptable salt or hydrate thereof according to claim 1, wherein:

$Z_1$, $Z_2$, $Z_3$, $Z_4$, $Z_5$, $Z_6$, $Z_7$, $Z_8$, $Z_9$ are independently selected from hydrogen atom, hydroxy, aldehyde group, carboxyl, amino, cyano, halogen, $C_1$-$C_3$ alkyl, $C_3$-$C_6$ cycloalkyl, $C_1$-$C_3$ alkoxy, $C_1$-$C_3$ alkylthiol, $C_3$-$C_6$ cycloalkoxy and $C_1$-$C_3$ alkyl-enyl.

* * * * *